United States Patent [19]
Arai et al.

[11] Patent Number: 5,340,498
[45] Date of Patent: Aug. 23, 1994

[54] ANTI-FERROELECTRIC LIQUID CRYSTAL AND LIQUID CRYSTAL DISPLAY DEVICE

[75] Inventors: Yoshihisa Arai, Tsukuba; tomoyuki Yui, Nagareyama; Yoshihiro Gocho, Tsukuba, all of Japan

[73] Assignee: Mitsubishi Gas Chemical Company, Inc., Tokyo, Japan

[21] Appl. No.: 108,448

[22] Filed: Aug. 19, 1993

[30] Foreign Application Priority Data

Aug. 19, 1992 [JP] Japan ................... 4-220175

[51] Int. Cl.$^5$ ............... C09K 19/12; C07C 69/72; C07C 43/13; G02F 1/13
[52] U.S. Cl. ................ 252/299.65; 560/62; 560/65; 560/83; 560/107; 568/643; 568/645; 359/103
[58] Field of Search .......... 252/299.01, 299.6, 299.64, 252/299.65, 299.67; 560/62, 65, 83, 107, 643, 645; 359/103

[56] References Cited
U.S. PATENT DOCUMENTS

| | | | |
|---|---|---|---|
| 5,108,650 | 4/1992 | Koden et al. | 252/299.01 |
| 5,167,861 | 12/1992 | Suzuki et al. | 252/299.65 |
| 5,184,847 | 2/1993 | Suzuki | 252/299.65 |
| 5,204,020 | 4/1993 | Suzuki et al. | 252/299.67 |

FOREIGN PATENT DOCUMENTS

| | | |
|---|---|---|
| 0219958 | 4/1987 | European Pat. Off. |
| 0301587 | 1/1989 | European Pat. Off. |
| 0484849 | 5/1992 | European Pat. Off. |

OTHER PUBLICATIONS

Database WPI Week 9135, Derwent Publications Ltd., London, GB; AN 91-257975 & JP-A-3 169 836 (Mitsubishi Kasei Corp.) Jul. 23, 1991.

*Primary Examiner*—Robert L. Stoll
*Assistant Examiner*—Shean C. Wu
*Attorney, Agent, or Firm*—Sherman and Shalloway

[57] ABSTRACT

A novel anti-ferroelectric liquid crystal of the formula (I),

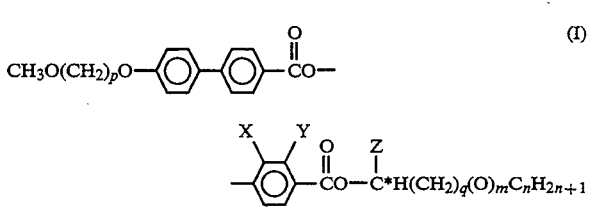

wherein:
is an integer of 3 to 8,
each of X and Y is independently a hydrogen atom or a fluorine atom,
Z is —CF$_3$, —CH$_3$ or —C$_2$H$_5$,
q is 0 or 5,
m is 0 or 1,
n is an integer of 2 to 8, and
C* is an asymmetric carbon, provided that when m is 0, q is 0 and n is an integer of 4 to 8 and that when m is 1, q is 5 and z is —CF$_3$, and use of tile above liquid crystal as a liquid crystal display device.

24 Claims, 24 Drawing Sheets

ANTI-FERROELECTRIC LIQUID CRYSTAL AND LIQUID CRYSTAL DISPLAY DEVICE

FIELD OF THE INVENTION

The present invention relates to a novel anti-ferroelectric liquid crystal and a liquid crystal display device using the same. The anti-ferroelectric liquid crystal provided by the present invention exhibits a fast response time. Further, it permits switching among tristable states and has distinct threshold characteristics and excellent memory characteristics. Therefore, it can be advantageously used as a liquid crystal display device.

PRIOR ART

Liquid crystal display devices have been and are applied to various small-size display devices due to their operationability at low voltages, low power consumption and performance of display with a thin screen. With the recent increase in application and use of liquid crystal display devices to/in the fields of information and office automation-related equipment and television, it is increasingly demanded to develop high-performance and large-size liquid crystal display devices having larger display capacity and higher quality than CRT display devices that have been so far available.

Liquid crystal devices that have been practically available use nematic liquid crystals. However, so long as the currently available nematic liquid crystals are used, it is difficult to increase the device size and decrease the production cost even when these nematic liquid crystals are applied to an active matrix liquid crystal display device employed in a liquid crystal television set, since the production process is complicated and the yield is low. Further, when the above nematic liquid crystals are applied to a simple matrix STN liquid crystal display device, it is not necessarily easy to drive a large-capacity display device, and the response time is limited. It is therefore difficult to display video rate. The nematic liquid crystal devices that are currently available hardly satisfy the above demands for achieving high-performance large-size display devices.

Under the above circumstances, it is a liquid crystal display device using a ferroelectric liquid crystal that is attracting attention as a liquid crystal display device having a fast response time. A surface-stabilized ferroelectric liquid crystal (SSFLC) device proposed by N. A. Clark and S. T. Lagerwall is attracting attention in that it has a remarkably fast response time and a wide viewing angle (N. A. Clark and S. T. Lagerwall. Appl. Phys. Lett. 36, 899 (1980). The switching characteristics of this SSFLC device have been studied in detail, and various ferroelectric liquid crystals have been synthesized to optimize various physical property parameters. However, the above ferroelectric liquid crystals have not yet been put to practical use for a variety of reasons described below. They are insufficient in "threshold characteristics". They are poor in contrast since their layer forming a ferroelectric phase has a chevron structure. It is difficult to realize a fast response time. It is difficult to achieve the bistability which is one of the most important characteristics of SSFLC, since it is difficult to control their molecular orientation. It is difficult to recover their orientation when the orientation is destroyed by mechanical shock.

Besides the above SSFLC, the development of devices having switching mechanisms different from that of SSFLC is also under way. One of these new switching mechanisms is a switching mechanism in a tristable states of a liquid crystal substance having an anti-ferroelectric phase (to be referred to as "anti-ferroelectric liquid crystal" hereinafter) (Japanese Journal of Applied Physics, Vol. 27, pp. L729, 1988).

The anti-ferroelectric liquid crystal has three stable states, i.e., two uniform states (Ur, Ul) observed in a ferroelectric liquid crystal and third state. Chandani et al have disclosed that this third state is an anti-ferroelectric phase (Japanese Journal of Applied Physics, Vo., 28, pp. L1261, 1989, Japanese Journal of Applied Physics, Vol. 28, pp. L1265, 1989). The switching among these three stable states is the first feature of the anti-ferroelectric liquid crystal. The second feature is that it exhibits a distinct threshold value against an applied voltage. Further, the third feature is that it has memory characteristics. These excellent features serve to produce a liquid crystal display device which can exhibit a fast response time and good contrast.

The anti-ferroelectric liquid crystal device has another important feature in that its layer structure undergoes relatively facile switching by an electric field (Japanese Journal of Applied Physics, Vol. 28, pp. L119, 1989, Japanese Journal of Applied Physics, Vol. 29, pp. L111, 1990). This feature serves to produce a liquid crystal display device which is almost free of defects and capable of self-restoring the molecular orientation and which is excellent in contrast. Anti-ferroelectric liquid crystals are already known as disclosed in Japanese Laid-open Patent Publications Nos. 213390/1989, 316339/1989, 316367/1989, 316372/1989 and 28128/1990 and Liquid Crystals, Vol. 6, pp. 167, 1989. The number of anti-ferroelectric liquid crystals that are so far known is not so large as that of ferroelectric liquid crystals since they have not yet been studied for a long time, but it is gradually increasing with an advance in studies thereof.

With regard to a response time, the problem of the anti-ferroelectric liquid crystals that have been so far synthesized is that it shows a slow response from a ferroelectric state to an anti-ferroelectric state. The anti-ferroelectric liquid crystals are somewhat disadvantageous in this regard as compared with conventional ferroelectric liquid crystals. For realizing a high resolution display device, therefore, it is greatly advantageous to provide an anti-ferroelectric liquid crystal which can exhibit two fast responses from an anti-ferroelectric state to a ferroelectric state and from a ferroelectric state to an anti-ferroelectric state around room temperature.

Figure 1:
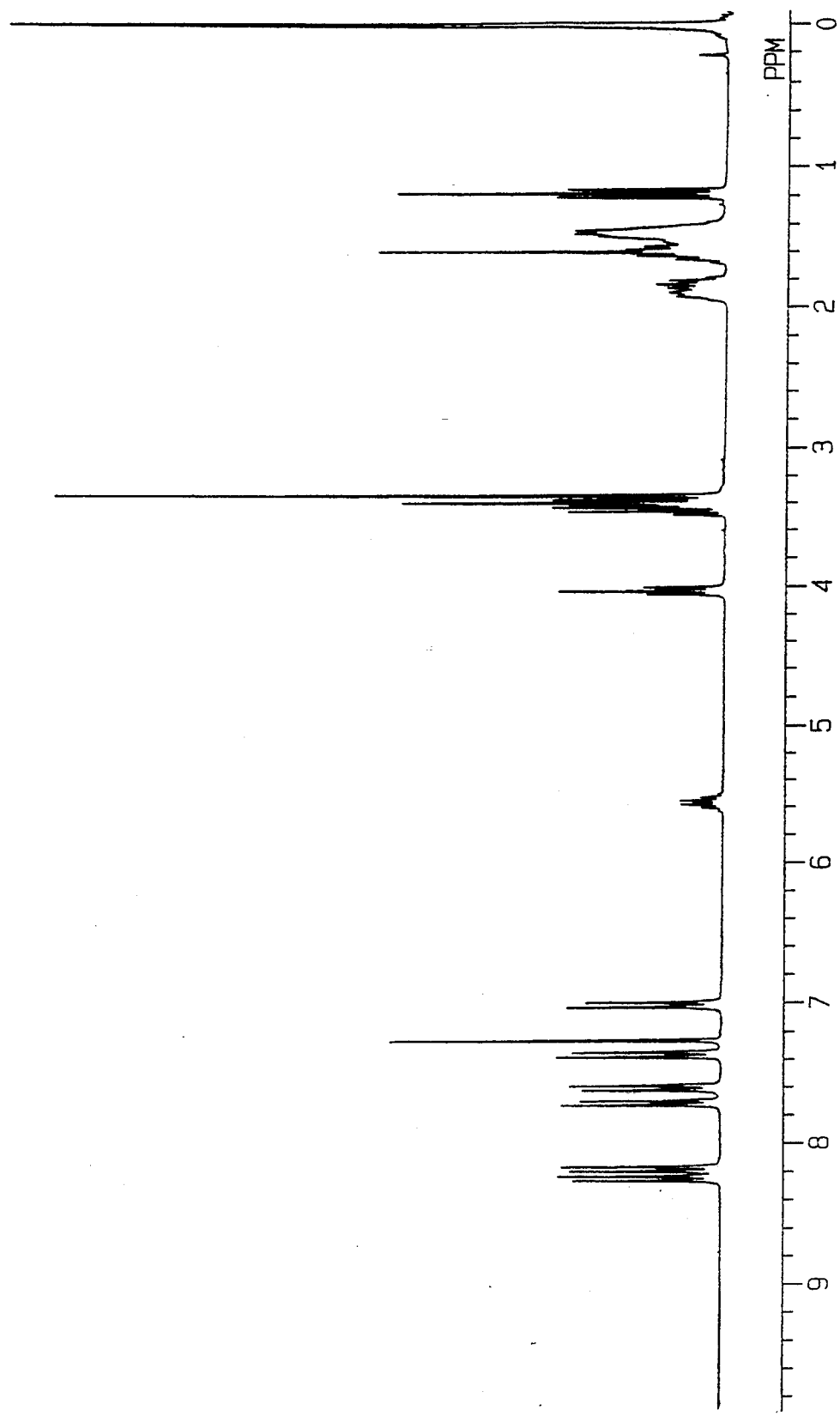
FIG. 1 shows the NMR spectrum of the liquid crystal obtained in Example 1.

The present invention has been made to cope with the above demand. It is therefore an object of the present invention to overcome the defect of the conventional anti-ferroelectric liquid crystals that they show slow response from a ferroelectric phase to an anti-ferroelectric phase, and to provide an anti-ferroelectric liquid crystal which exhibits a very fast response.

According to the present invention, the above object of the present invention can be achieved by an anti-ferroelectric liquid crystal of the formula (I),

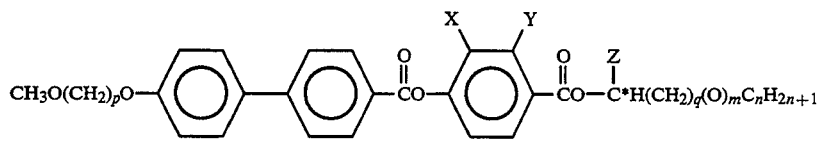

(I)

wherein:
p is an integer of 3 to 8,
each of X and Y is independently a hydrogen atom or a fluorine atom,
Z is $-CF_3$, $-CH_3$ or $-C_2H_5$,
q is 0 or 5,
m is 0 or 1,
n is an integer of 2 to 8, and
C* is an asymmetric carbon, provided that when m is 0, q is 0 and n is an integer of 4 to 8 and that when m is 1, q is 5 and z is $-CF_3$,
and a liquid crystal display device to which the above anti-ferroelectric liquid crystal is applied.

Typical compounds of the diphenyl ester type anti-ferroelectric liquid crystals that have been so far synthesized have the following formula (A),

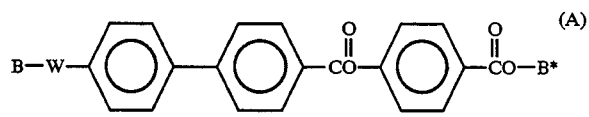

(A)

wherein:
B is a linear alkyl group,
W is a single bond,

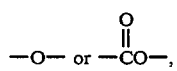

and
B* is an optically active group.

In the compounds of the above formula (A), generally, B is mainly a linear alkyl group having at least 3 carbon atoms. In the compounds of the above formula (A), the response time (V-1) from an anti-ferroelectric state to a ferroelectric state is very fast, while the response time (V-II) from a ferroelectric state to an anti-ferroelectric state is very slow. For example, V-II is 10 to 100 times as large as V-I. In particular, the response time (V-II) from a ferroelectric state to an anti-ferroelectric state when the voltage is brought back to zero (0) V is approximately 200 to 2,000 microseconds.

For applying the liquid crystal of the above formula (A) to a liquid crystal display device, the defect of a slow response time can be improved to some extent by a driving method such as formulation of a driving waveform. However, when it is applied to a display having 480 or more scanning lines, flickering occurs, and in fact, it is difficult to realize a practical display having high resolution. In the field of anti-ferroelectric liquid crystals, therefore, it has been one essential object to improve the response time from a ferroelectric state to an anti-ferroelectric state.

The present inventors have focussed on the substituent B of the compounds of the above formula (A). That is, it has been found that the response time from a ferroelectric state to an anti-ferroelectric state can be remarkably decreased by replacing the linear alkyl group as the substituent B with a methoxyalkylene group. On the basis of this finding, the present invention has been completed.

Further studies by the present inventors have also revealed that not only the response time (V-II) from a ferroelectric state to an anti-ferroelectric state can be decreased but also the response time (V-I) from an anti-ferroelectric state to a ferroelectric state can be considerably decreased by replacing the substituent B with a methoxyalkylene group as described above and selecting a specifically structured group as the optically active group B* (chiral portion).

The liquid crystal of the above formula (I), provided by the present invention, will be detailed hereinafter.

As described above, the liquid crystal of the present invention has one structural feature in that it has the methoxyalkylene group of $(CH_3O(CH)_p-)$ positioned on the left hand side of the formula (I). Due to this structural feature, the liquid crystal of the present invention exhibits a very fast response time, as will be made clear by Examples and Comparative Examples to be described later. And, due to a combination of the structure on the left hand side of the formula (I) with a structure in other portion, particularly the optically active portion (chiral portion), the liquid crystal of the present invention exhibits further excellent properties.

In the above formula (I), Z is preferably $-CF_3$ or $-CH_3$, p is preferably an integer of 4, 6 or 8, X is preferably a hydrogen atom, and Y is preferably a hydrogen atom or a fluorine atom.

The preferred liquid crystal of the present invention is classified into two types concerning whether or not it contains an ether bond ($-O-$) in the optically active (chiral) portion.

That is, the liquid crystal of one type containing an ether bond in the optically active portion is a liquid crystal of the formula (I) in which m is 1, q is 5, Z is $-CF_3$ and n is 2. As the liquid crystal of this type, preferred is a liquid crystal of the formula (I) in which X is a hydrogen atom and Y is a hydrogen atom or a fluorine atom, and more preferred is a liquid crystal of the formula (I) in which p is 4, 6 or 8, particularly 6 or 8.

The liquid crystal of the other type containing no ether bond in the optically active portion is a liquid crystal of the formula (I) in which m and q are both zero, Z is $-CF_3$ or $-CH_3$ and n is 4 or 6. As the liquid crystal of this type, preferred is a liquid crystal of the formula (I) in which n is 6, and more preferred is a liquid crystal of the formula (I) in which X is a hydrogen atom and Y is a hydrogen atom or a fluorine atom.

The process for synthesizing the anti-ferroelectric liquid crystal of the formula (I) will be explained hereinafter, although the present invention shall not be limited thereto.

First, optically active alcohols $[HOC*H(Z)(CH_2)_q(O)_mC_nH_{2n+1}]$ are used for synthesizing the liquid crystal of the present invention. Optically active alcohols such as R-(+)-1,1,1-trifluoro-2-octanol, R-

(−)-2-octanol and S-(+)-3-nonanol are commercially available. Optically active alcohols having high optical purity such as R-(+)-1,1,1-trifluoro-7-ethoxy-2-heptanol can be produced by the following reaction processes.

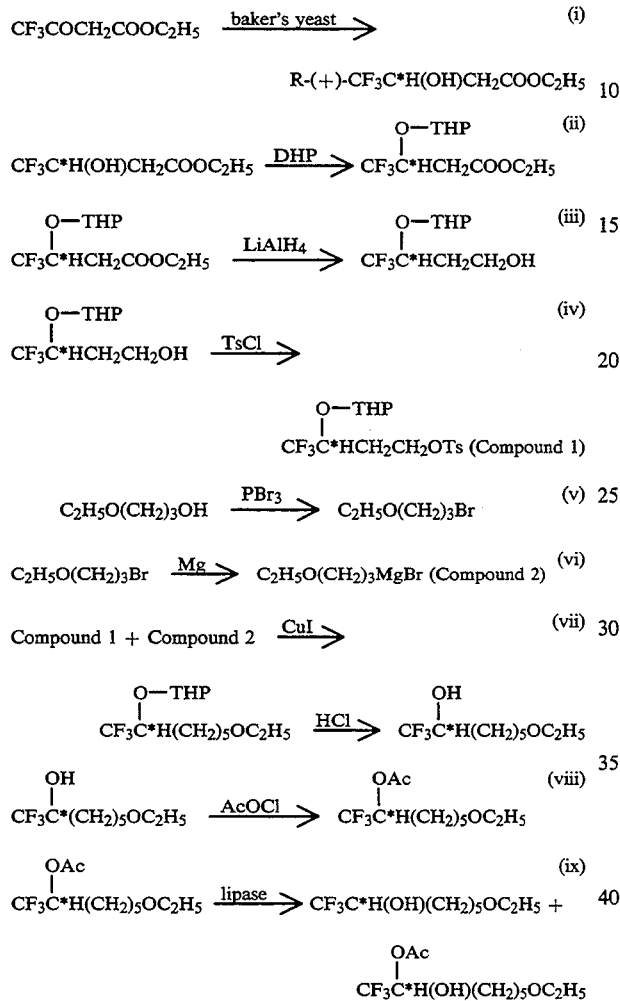

In the above reaction processes (i) to (ix) for producing optically active alcohols, the symbols refer to the following.
DHP: dihyropyrane
THP: tetrahydropyrane
Ts: tosyl group
Ac: acetyl group The liquid crystal of the formula (I) is produced, for example, by the following reaction processes.

$$HO(CH_2)_pOH + CH_3I + Na \longrightarrow CH_3O(CH_2)_pOH \quad (x)$$

$$CH_3O(CH_2)_pOH + PBr_3 \longrightarrow CH_3O(CH_2)_pBr \quad (xi)$$

$$CH_3O(CH_2)_pBr + HO-Ph-Ph-COOH + KOH \longrightarrow CH_3O(CH_2)_pO-Ph-Ph-COOH \quad (xii)$$

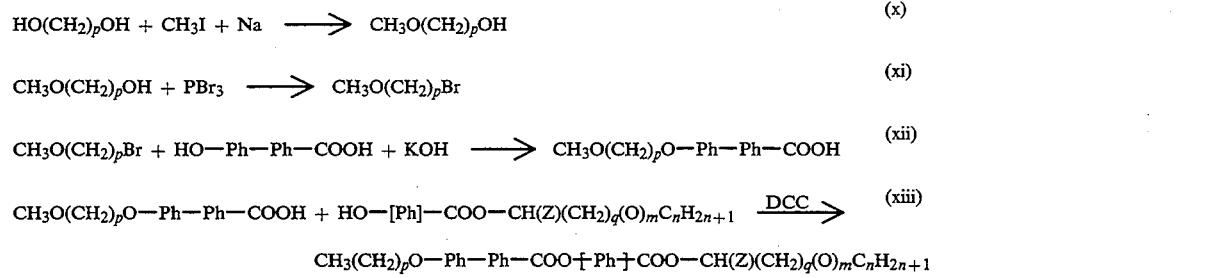

In the above reaction processes (x) to (xiii), the same symbols as those used in the formula (I) refer to the same meanings as those in the formula (I), and the remaining symbols refer to the following.

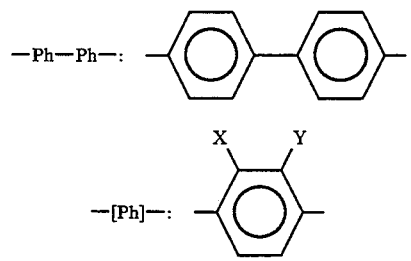

DCC: Dicyclohexylcarbodiimide

The anti-ferroelectric liquid crystal of the present invention, represented by the formula (I), exhibits a very fast response time, and can give an excellent liquid crystal display device utilizing said property.

The present invention can provide a novel anti-ferroelectric liquid crystal. The novel antiferroelectric liquid crystal provided by the present invention exhibits a very fast response time, and excels particularly in a response time from an anti-ferroelectric state to a ferroelectric state. And, it can be used in a liquid crystal device owing to its properties such as switching among tristable states, distinct threshold characteristics and excellent memory characteristics.

The present invention will be explained more in detail hereinafter by reference to Examples and Comparative Examples, although the present invention shall not be limited thereto.

EXAMPLE 1

Production of R-4-(1-trifluoromethyl-6-ethoxyhexycarbonylphenyl) 4'-methoxyhexyloxybiphenyl)-4-carboxylate (compound of the formula (I) wherein p=6, X=H, Y=H, Z=CF$_3$, q=5, m=1, and n=2)

(1) Production of 6-methoxy-1-hexanol

150 Grams (1.27 mol) of 1,6-hexanediol was added to 400 ml of tetrahydrofuran, and further, 9.7 g (0.42 mol) of sodium was added. After the sodium was completely dissolved, 62.3 g (0.44 mol) of methyl iodide was added dropwise. The mixture was stirred for 7 hours, and then the reaction mixture was treated with water and subjected to extraction with ether. The extract was dried over anhydrous sodium sulfate, concentrated and purified by distillation. Boiling point 136°–140° C. (40 Torr) Yield 39%.

(2) Production of 1-bromo-6-methoxyhexane 27.7 Grams (0.1 mol) of phosphorus tribromide was slowly dropwise added to 31.2 g (0.24 mol) of 6-methoxy-1-hexanol. The mixture was stirred for 4 hours, and then allowed to stand overnight. Water was added, and the mixture was subjected to extraction with hexane. The extract was washed with water, with an alkaline aqueous solution and with a saturated sodium chloride aqueous solution, and then dried over anhydrous sodium sulfate. The dried extract was concentrated and then purified by distillation. Boiling point 76° C. (15 Torr). Yield 33%.

(3) Production of 4'-methoxyhexyloxy-biphenyl-4-carboxylic acid.

8.4 Grams of 1-bromo-6-methoxyhexane and 4.5 g of 4'-hydroxybiphenyl-4-carboxylic acid were refluxed in 100 ml of water and 400 ml of ethanol for 4 hours. Concentrated hydrochloric acid was added to the reaction mixture so that the mixture showed pH 1, then 150 ml of water was added, and the resultant mixture was refluxed for 1 hour. The reaction mixture was cooled to precipitate a crystal, and the crystal was recovered by filtration. The so-obtained crystal was recrystallized from acetone. Yield 55%.

(4) Production of 4-(1-trifluoromethyl-6-ethoxyhexyloxycarbonylphenyl) 4'-methoxyhexyloxybiphenyl-4-carboxylate 1 Gram of 4'-methoxyhexyloxybiphenyl-4-carboxylic acid, 0.82 g of 4-hydroxy-1-trifluoromethyl-6-ethoxyhexyloxycarbonylphenyl and 0.5 g of dimethylaminopyridine were dissolved in 10 ml of tetrahydrofuran. A solution of 0.66 g of dicyclohexylcarbodiimide (DCC) in 5 ml of tetrahydrofuran was added dropwise, and the mixture was stirred at room temperature for 4 hours.

Tetrahydrofuran was distilled off, and the residue was subjected to a silica gel column for separation and purification to give the intended product. Yield 50%.

FIG. 1 shows the NMR spectrum of the intended product. The phase identification was carried out by texture observation and DSC measurement.

The phase sequence of the above-obtained compound was as follows. This compound was found to be a liquid crystal having an anti-ferroelectric phase.

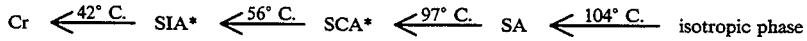

In the above phase sequence, SA stands for a smectic A phase, SCA* stands for an anti-ferroelectric smectic C phase, and SIA* stands for an anti-ferroelectric smectic I phase.

(5) Measurements of physical properties

Figure 2:
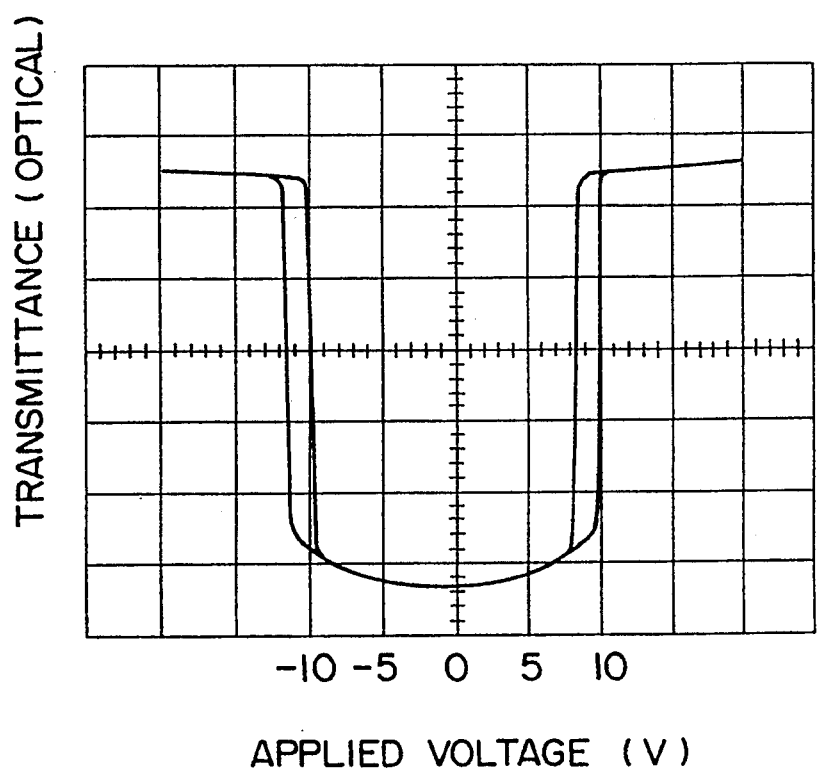
FIG. 2 shows the optical response hysteresis of the liquid crystal obtained in Example 1.

An ITO electrode-attached liquid crystal cell (cell thickness 2 μm) which had a rubbing-treated thin polyimide film was charged with the above compound in an isotropic state. The liquid crystal was aligned in an SA phase by gradually cooling the cell at a rate of 1.0° C./minute. The cell was placed between polarizing plates at right angles with the cell such that the direction of liquid crystal layer was parallel with an analyzer or a polarizer. While a triangular wave voltage at ±40 V and 0.2 Hz was applied, the cell was measured for a change in transmittance with a photomultiplier. As a result, double hysteresis peculiar to an anti-ferroelectric phase was found in the temperature range of from 97° C. to 56° C. FIG. 2 shows an optical response hysteresis at 60° C.

Further, the response time was defined as a time required for a change in the transmittance from 10 to 90%, and the response time was measured by applying a stepwise voltage having a frequency of 30 Hz at 25 V to show very fast response characteristics. That is, the response time from an anti-ferroelectric phase to a ferroelectric phase at 85° C. was 5 microseconds, and the response time from a ferroelectric phase to an anti-ferroelectric phase at 85° C. was 3 microseconds.

EXAMPLES 2-4

Production of R-4-(1-trifluoromethyl-heptyloxycarbonylphenyl) 4'-methoxyhexyloxybiphenyl-4-carboxylate (compound of the formula (I) in which p=6, X=H, Y=H, Z=CF₃, q=0, m=0 and n=6), R-4-(1-methylheptyloxycarbonylphenyl) 4'-methoxyhexyloxybiphenyl-4-carboxylate (compound of the formula (I) in which p=6, X=H, Y=H, Z=CH₃, q=0, m=0 and n=6) and S-4-(1-ethyl-heptyloxycarbonylphenyl) 4'-methoxyhexyloxybiphenyl-4-carboxylate (compound of the formula (I) in which p=6, X=H, Y=H, Z=C₂H₅, q=0, m=0 and n=6)

Liquid crystals were produced in the same manner as in Example 1 except that the R-4-hydroxy-1- trifluoromethyl-6-ethoxyhexyloxycarabonylphenyl was replaced with R-4-hydroxy-1-trifluoromethyl-heptyloxycarbonylphenyl, R-4-hydroxy-1-methyl-heptyloxycarbonylphenyl and S-4-hydroxy-1-ethyl-heptyloxycarbonylphenyl. The so-obtained liquid crystals were evaluated for physical properties in the same manner as in Example 1.

Figure 3:
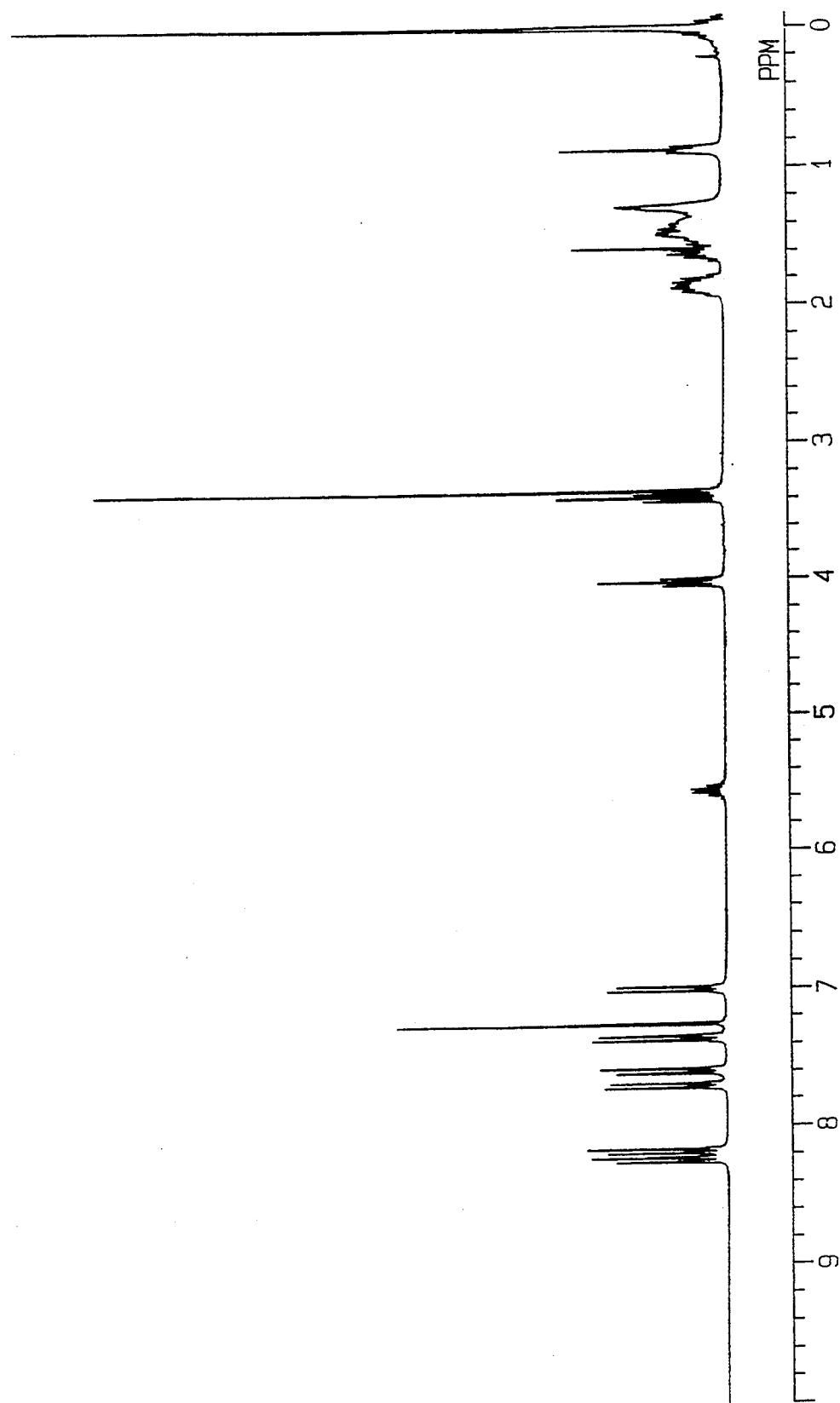
FIGS. 3 to 17 show the NMR spectra of the liquid crystals obtained in Examples 2 to 16.
Figure 4:
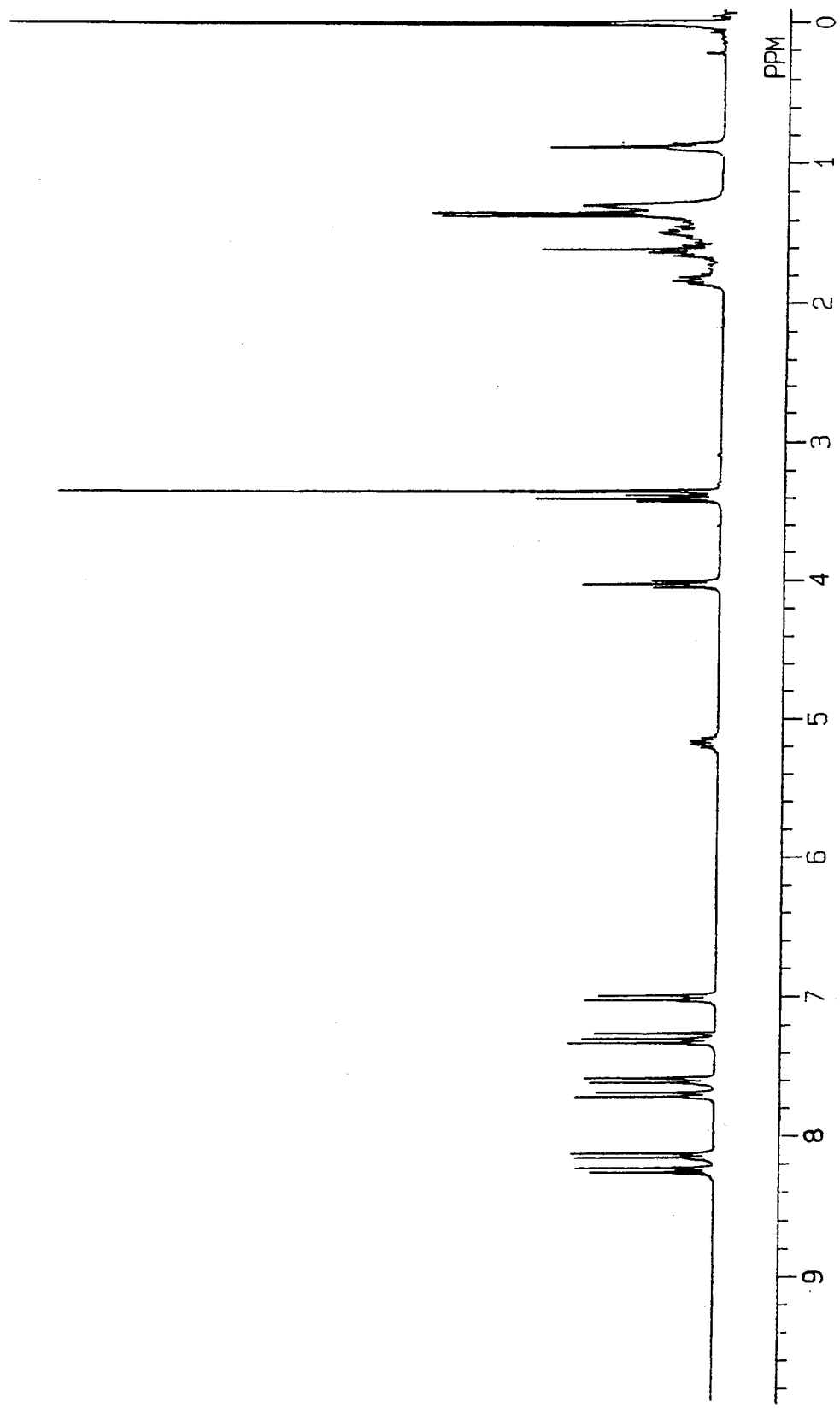
Figure 5:
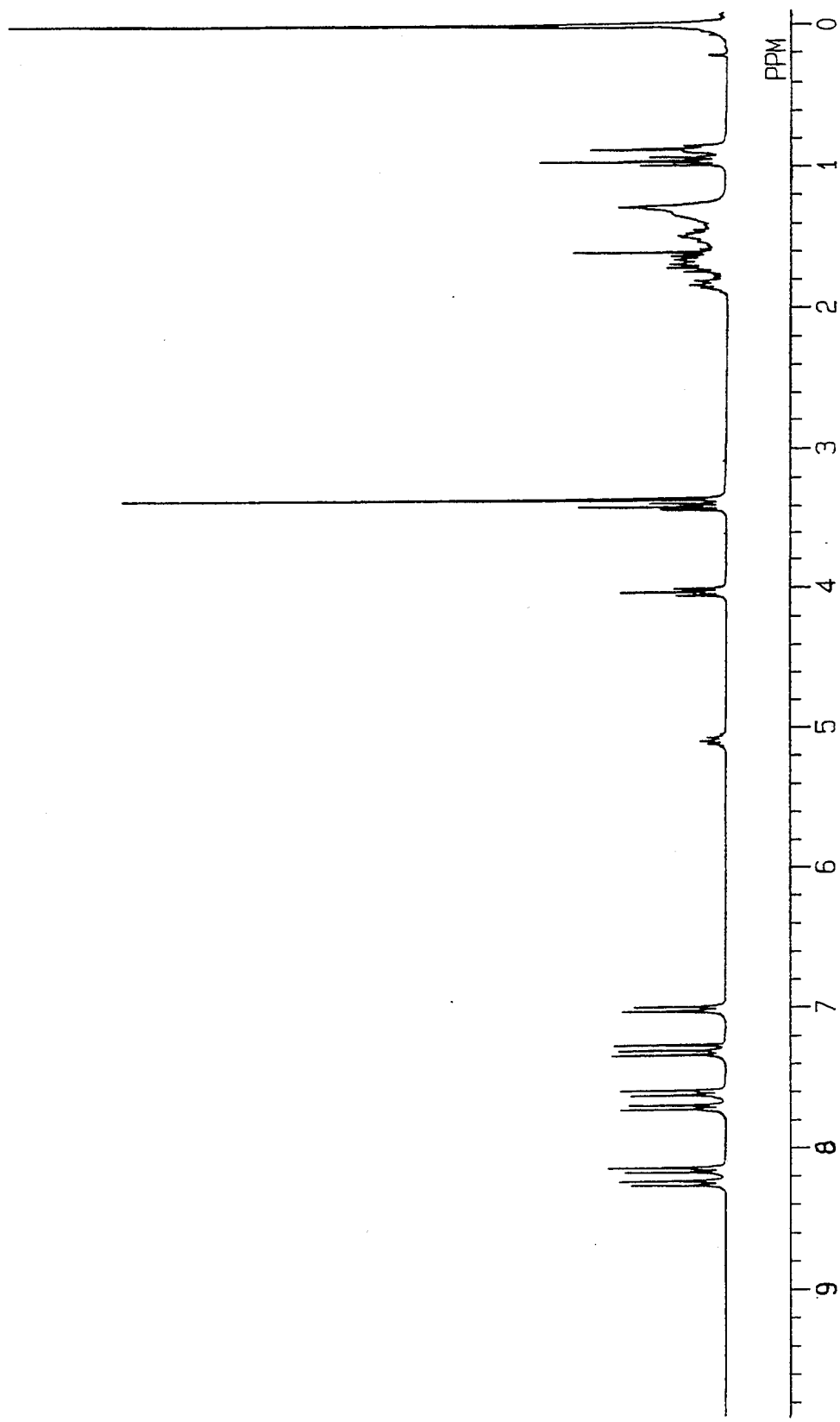

FIG. 3 to 5 shows the NMR spectra of the above liquid crystals obtained in Examples 2 to 4. Table 1 shows the physical properties of the above liquid crystals.

TABLE 1

| | Physical properties in CH₃O(CH₂)₆—O—Ph—Ph—COO—Ph—R* | | |
|---|---|---|---|
| R* | Phase sequence | | Response time μ second |
| Example 2 —C*H(CF₃)C₆H₁₃ | CR ⟵59° C.⟶ SIA* ⟵69° C.⟶ SCA* ⟵116° C.⟶ SA ⟵125° C.⟶ Iso | | 9,4 (106° C.) |
| Example 3 —C*H(CH₃)C₆H₁₃ | CR ⟵38° C.⟶ SIA* ⟵71° C.⟶ SCA* ⟵97° C.⟶ SA ⟵137° C.⟶ Iso | | 4,36 (87° C.) |
| Example 3 —C*H(C₂H₅)C₆H₁₃ | CR ⟵21° C.⟶ SX ⟵58° C.⟶ SCA* ⟵90° C.⟶ SA ⟵113° C.⟶ Iso | | 17,334 (80° C.) |

In the heading of Table 1, Ph stands for a phenyl group. In Table 1, Cr stands for a crystal phase, Iso stands for an isotropic phase, and SX stands for an unidentified phase. In the column of "Response time", the first values show a response time from an anti-ferroelectric phase to a ferroelectric phase, and the second values show a response time from a ferroelectric phase to an anti-ferroelectric phase. The parenthesized values show temperatures for the measurement.

EXAMPLE 5

Production of 3-fluoro-4-(1-trifluoromethyl-6-ethoxyhexyloxycarbonylphenyl) 4'-methoxyhexyloxybiphenyl-4-carboxylate (compound of the formula (I) in which p=6, X=H, Y=F, Z=CF$_3$, q=5, m=1 and n=2)

The above compound was produced in the same manner as in Example 1 except that the 4-hydroxy-1-trifluoromethyl-6-ethoxyhexyloxycarbonylphenyl was replaced with 3-fluoro-4-hydroxy-1-trifluoromethyl-6ethoxyhexyloxycarbonylphenyl.

Figure 6:
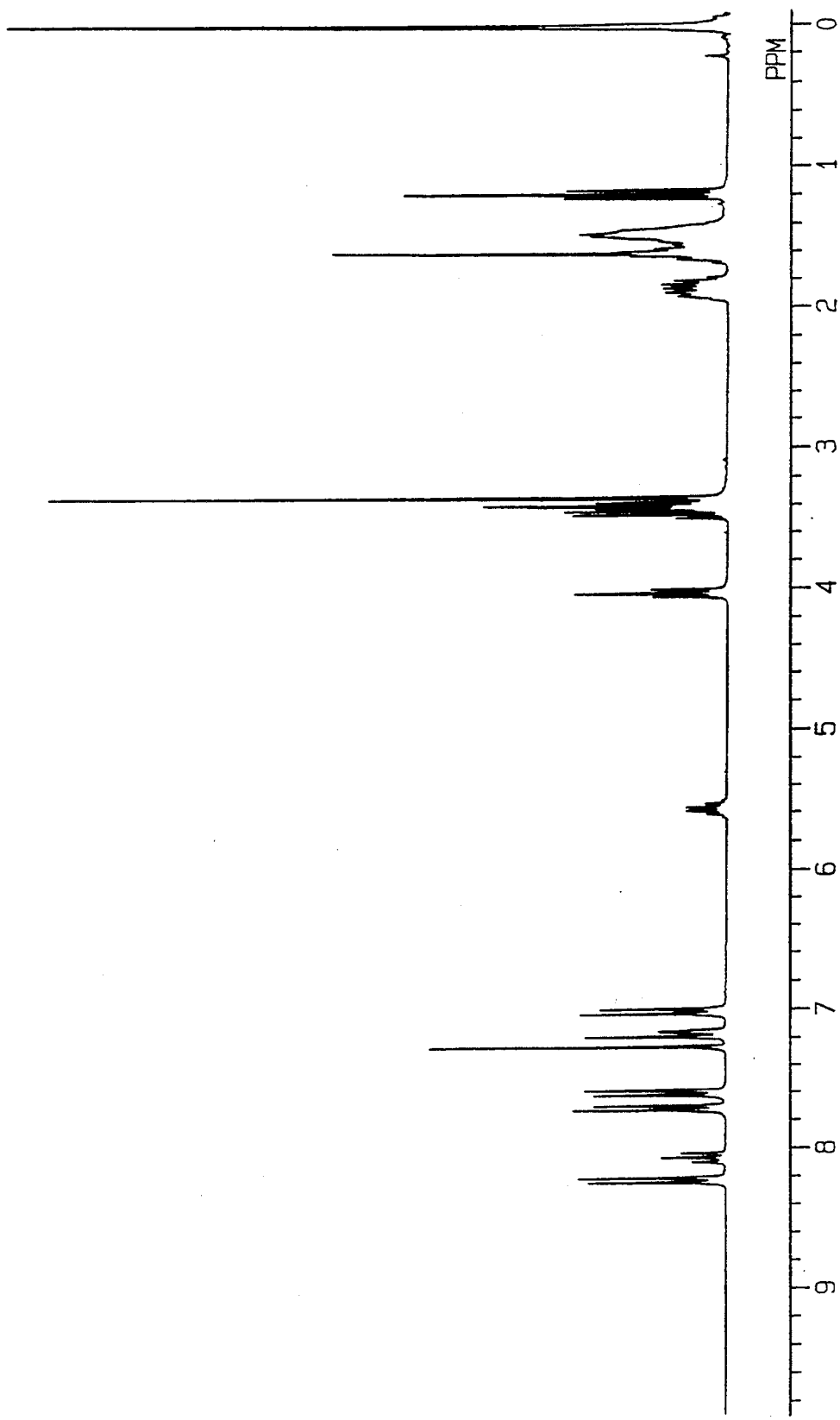
Figure 7:
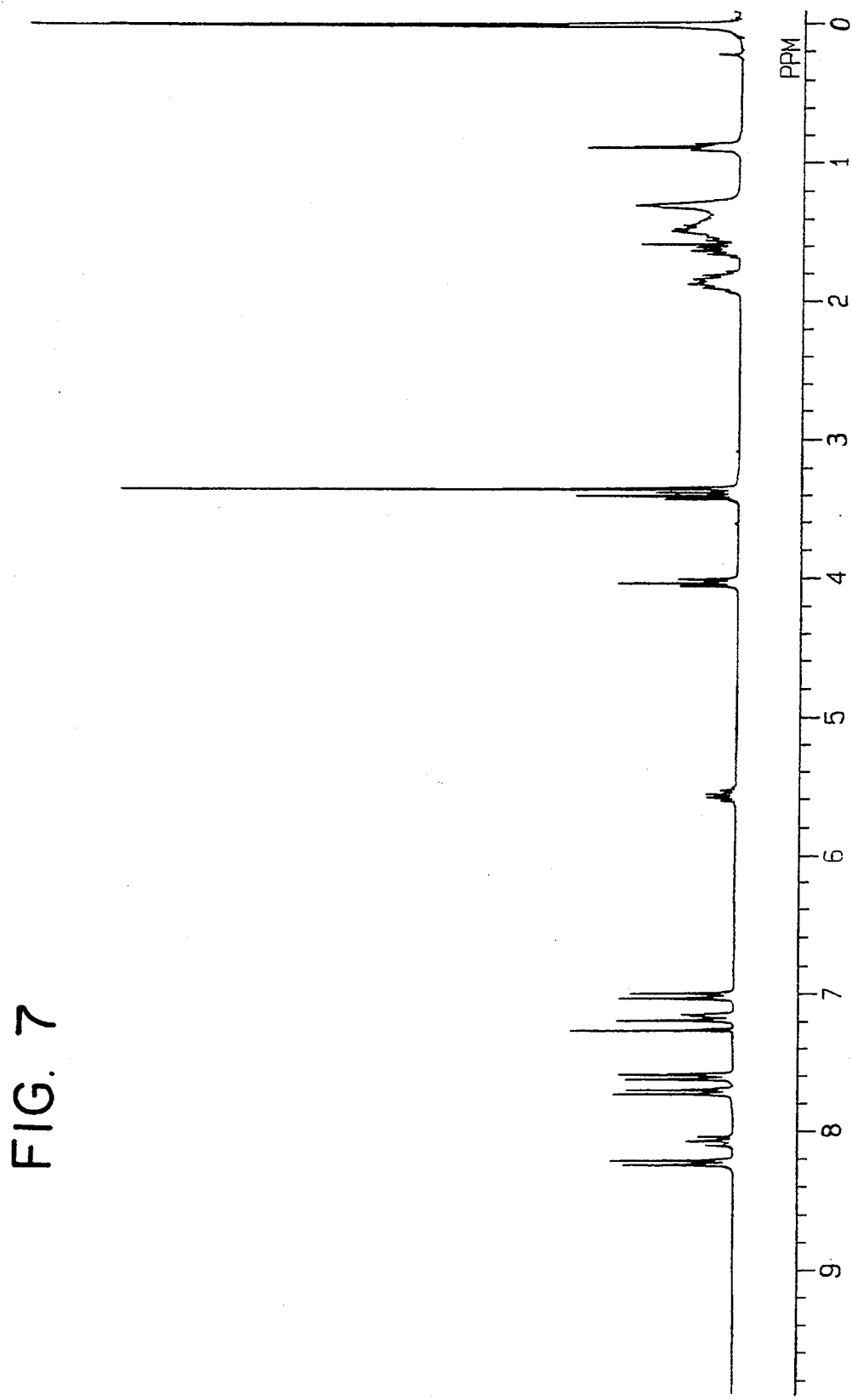
Figure 8:
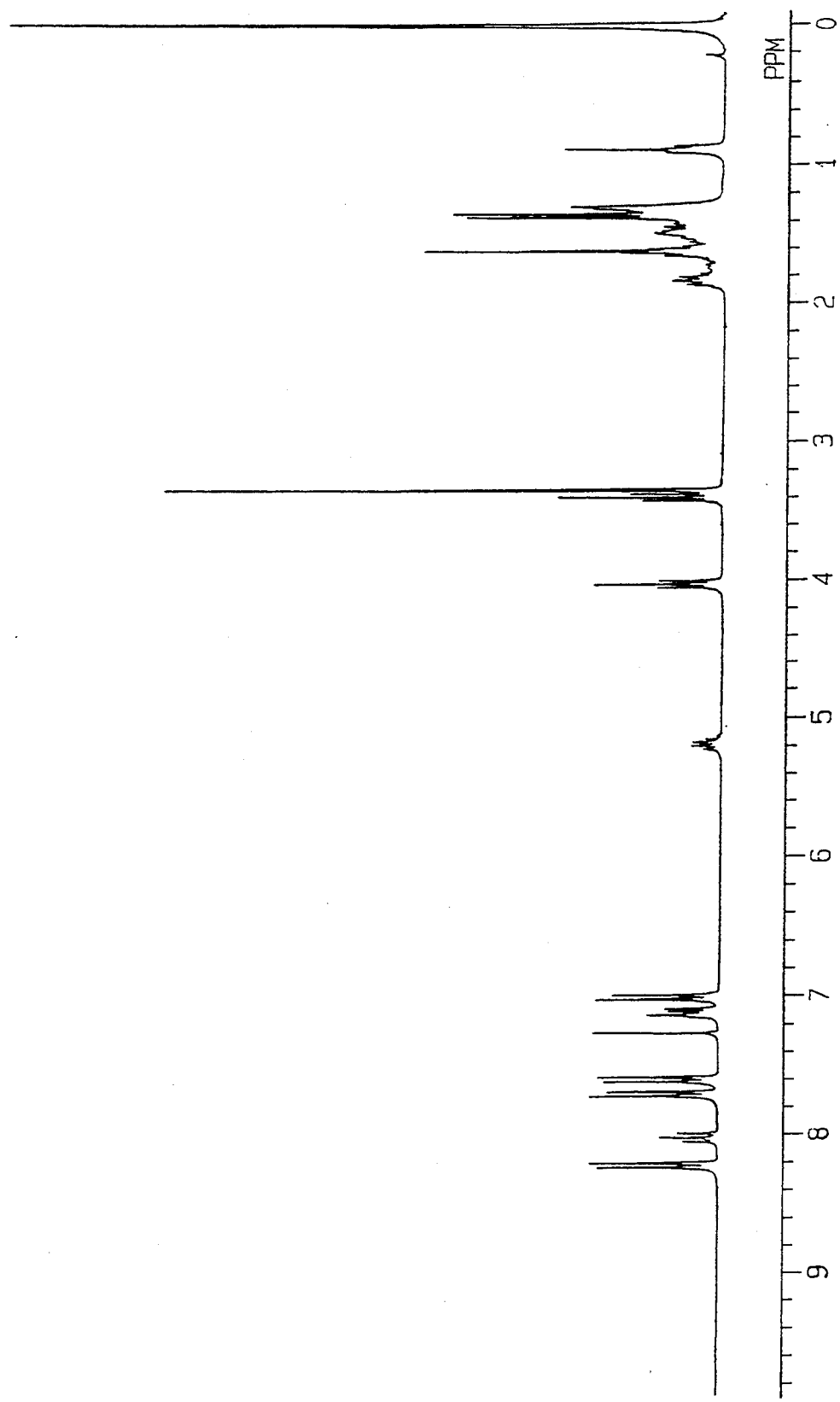
Figure 9:
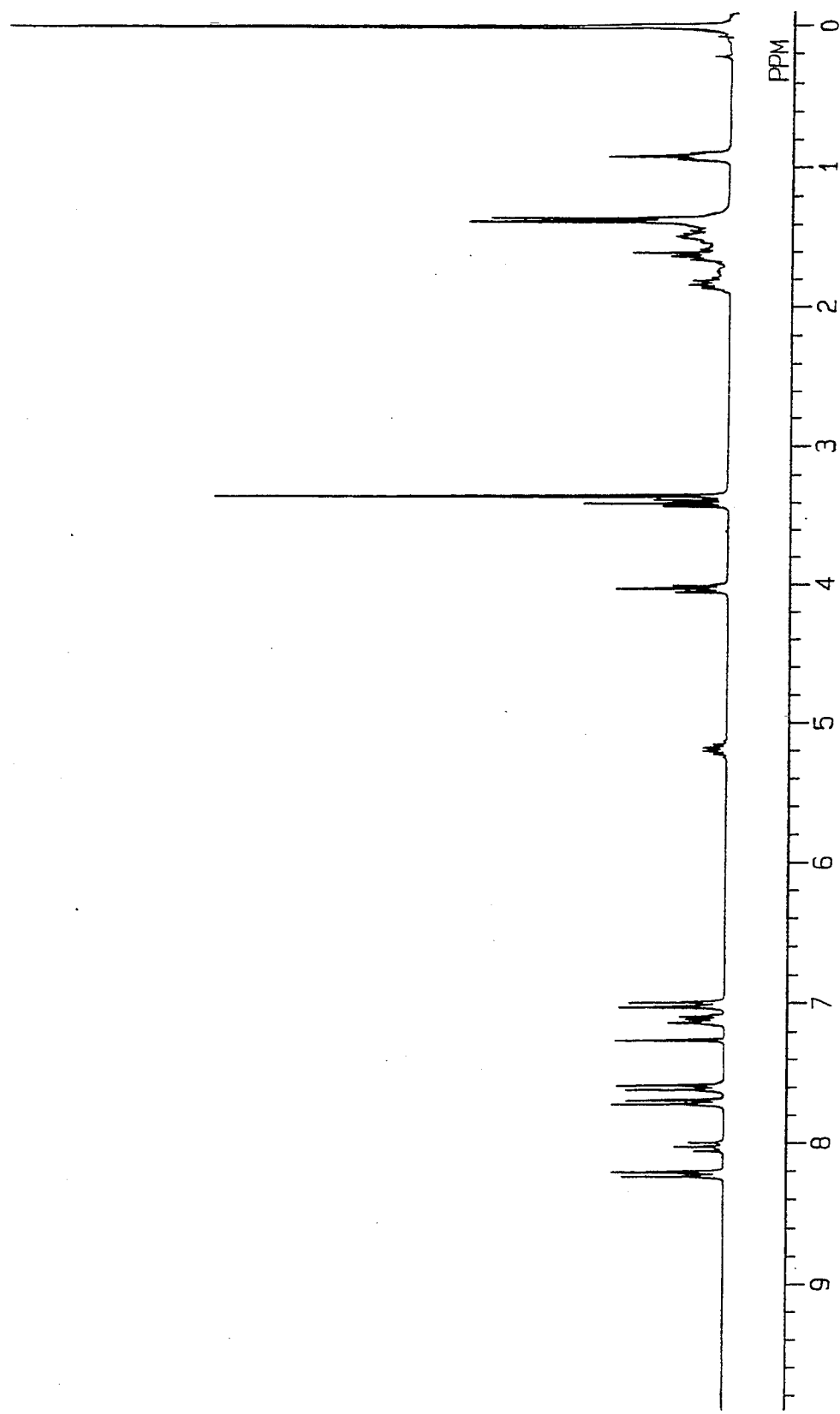
Figure 10:
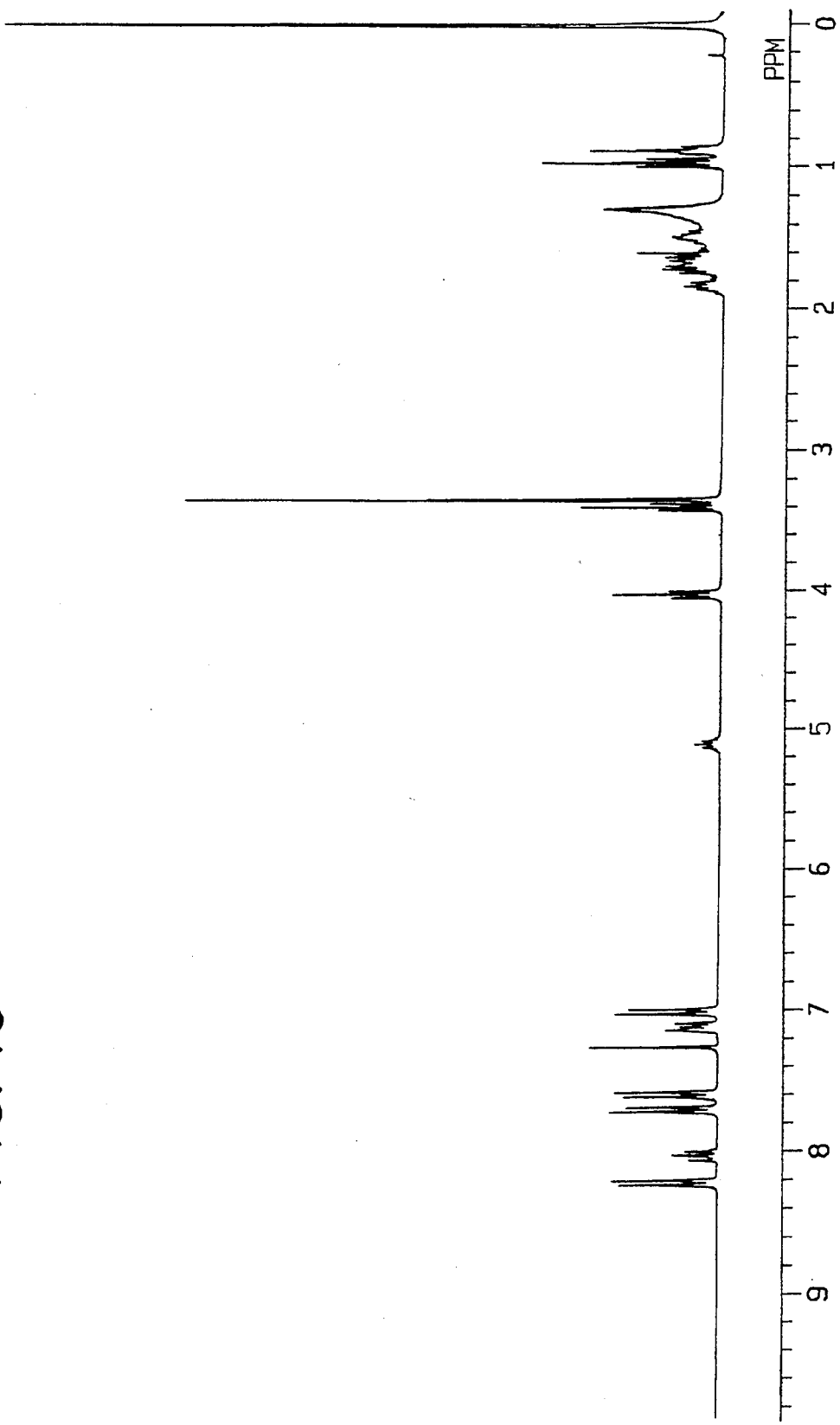

FIG. 6 shows the NMR spectrum of the so-obtained compound. The phase identification thereof was carried out by texture observation and DSC measurement.

The phase sequence of the above compound was as follows. This compound was found to be a liquid crystal having an anti-ferroelectric phase.

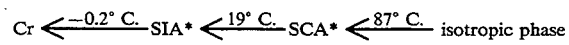

When the above compound was evaluated for an optical response in the same manner as in Example 1, item (5), double hysteresis peculiar to an anti-ferroelectric phase was found in the temperature range of from 87° C. to 19° C. Further, the above compound was measured for a response time in the same manner as in Example 1, item (5), to show very fast response characteristics. That is, the response time from an anti-ferroelectric phase to a ferroelectric phase at 77° C. was 11 microseconds, and the response time from a ferroelectric phase to an anti-ferroelectric phase at 77° C. was 4 microseconds.

EXAMPLES 6-9

Production of 3-fluoro-4-(1-trifluoromethyl-heptyloxycarbonylphenyl)4'-methoxyhexyloxbiphenyl-4-carboxylate (compound of the formula (I) in which p=6, X=H, Y=F, Z=CF$_3$, q=0, m=0 and n=6), 3-fluoro-4-(1-methyl-6-heptyloxycarbonylphenyl) 4'-methoxyhexylobiphenyl-4-carboxylate methoxyhexyloxybiphenyl-4-carboxylate (compound of the formula (I) in which p=6, X=H, Y=F, Z=CH$_3$, q=0, m=0 and n=6), 3-fluoro-4-(1-methyl-pentyloxycarbonylphenyl) 4'-methoxyhexyloxybiphenyl-4-carboxylate (compound of the formula (I) in which p=6, X=H, Y=F, Z=CH$_3$, q=0, m=0 and n=4), and 3-fluoro-4-(1-ethyl-6-heptyloxycarbonyl-phenyl) 4'-methoxyhexyloxybiphenyl-4-carboxylate (compound of the formula (I) in which p=6, X=H, Y=F, Z=C$_2$H$_5$, q=0, m=0 and n=6).

The above compounds were produced in the same manner as in Example 5 except that the 3-fluoro-4-hydroxyl-1-trifluoromethyl-6-ethoxyhexyloxycarbonylphenyl was replaced with 3-fluoro-4-hydroxy-1-trifluoromethyl-6-heptyloxycarbonylphenyl, 3-fluoro-4-hydroxy-1-methylheptyloxycarbonylphenyl), 3-fluoro-4-hydroxy-1-methylpentyloxycarbonylphenyl) and 3-fluoro-4-hydroxy-1-ethyl-heptyloxycarbonylphenyl).

FIGS. 7 to 10 show the NMR spectra of the compounds obtained in Examples 6 to 9. The phase identification thereof was carried out by texture observation and DSC measurement.

Table 2 shows the results of their physical property measurements.

TABLE 2

| | Physical properties in CH$_3$O(CH$_2$)$_6$—O—Ph—Ph(3-F)—COO—Ph—R* | |
|---|---|---|
| R* | Phase sequence | Response time μ second |
| Example 6 —C*H(CF$_3$)C$_6$H$_{13}$ | CR ←12° C.— SIA* ←27° C.— SCA* ←105° C.— Iso | 14,24 (96° C.) |
| Example 7 —C*H(CH$_3$)C$_6$H$_{13}$ | CR ←−0.4° C.— SIA* ←29° C.— SCA* ←108° C.— SA ←132° C.— Iso | 24,8 (98° C.) |
| Example 8 —C*H(CH$_3$)C$_4$H$_9$ | CR ←2° C.— SIA* ←31° C.— SCA* ←112° C.— SA ←138° C.— Iso | *1 |
| Example 9 —C*H(C$_2$H$_5$)C$_6$H$_{13}$ | CR ←?— SX ←31° C.— SCA* ←92° C.— SA ←103° C.— Iso | 200,95 (80° C.) |

*1. Since the threshold voltage was as high as 70 V or more, response time was not measured.

In the above Table 2, 3-F stands for fluorine substituted on the 3-position of a phenyl group.

EXAMPLE 10

Production of 2-fluoro-4-(1-trifluoromethyl-6-ethoxyhexyloxycarbonylphenyl) 4'-methoxyhexyloxybiphenyl-4-carboxylate (compound of the formula (I) in which p=6, X=F, Y=H, Z=CF$_3$, q=5, m=1 and n=2)

The above compound was produced in the same manner as in Example 1 except that the 4-hydroxy-1-trifluoromethyl-6-ethoxyhexyloxycarbonylphenyl was replaced with 2-fluoro-4-hydroxy-1-trifluoromethyl-6-ethoxyhexyloxycarbonylphenyl.

Figure 11:
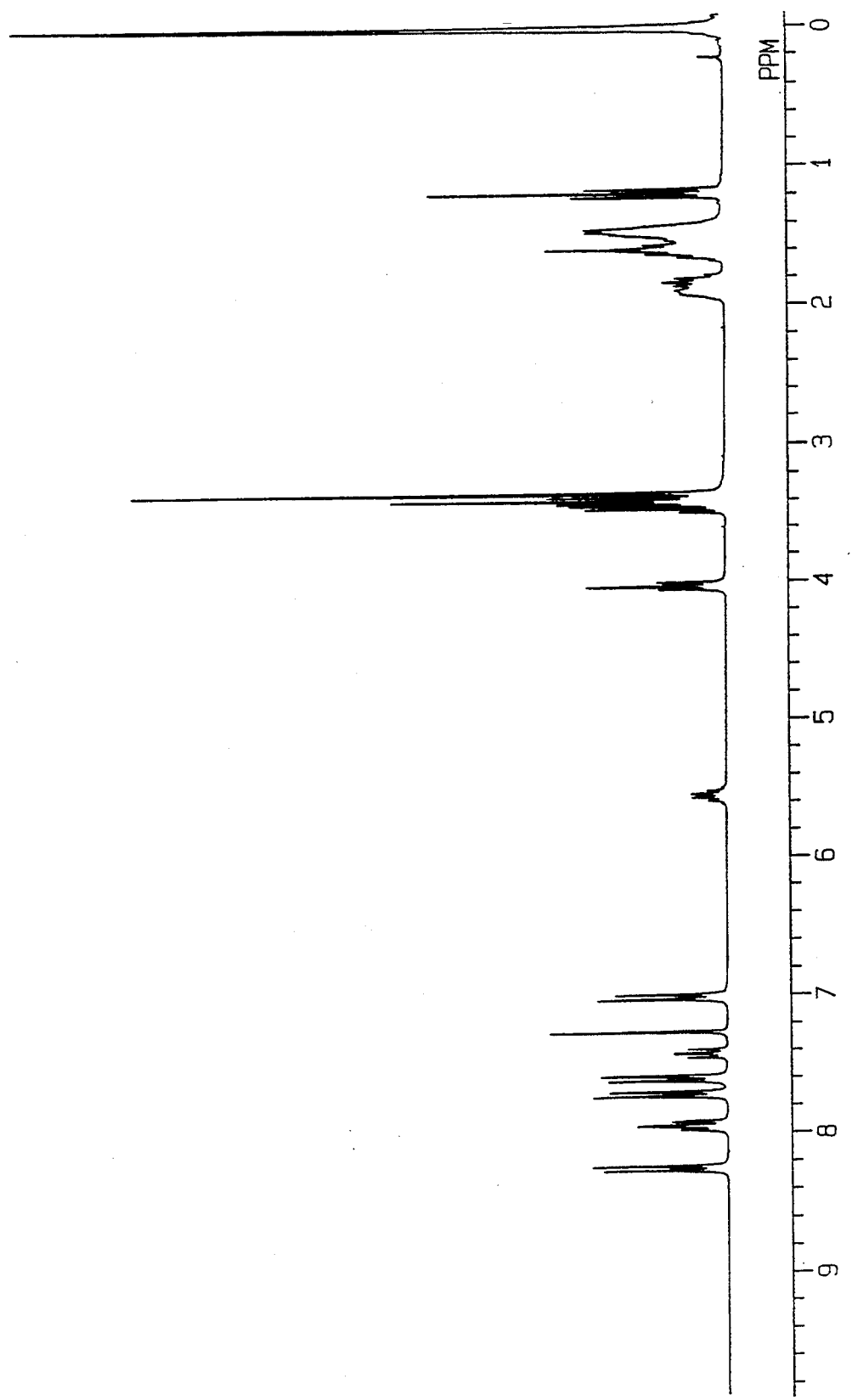

FIG. 11 shows the NMR spectrum of the so-obtained compound. The phase identification thereof was carried out by texture observation and DSC measurement.

The phase sequence of the above compound was as follows. This compound had an anti-ferroelectric phase and hence, was found to be a liquid crystal having an anti-ferroelectric phase.

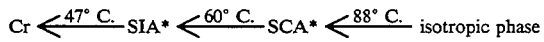

EXAMPLE 11

Production of R-4-(1-trifluoromethyl-6-ethoxyhexycarbonylphenyl) 4'-methoxybutyloxybiphenyl-4-carboxylate (compound of the formula (I) in which p=4, X=H, Y=H, Z=CF$_3$, q=5, m=1 and n=2)

(1) Production of 1-bromo-4-methoxybutane

To 25 grams (0.24 mol) of 4-methoxy-1-butanol was slowly dropwise added 27.7 g (0.1 mol) of phosphrus tribromide. The mixture was stirred for 4 hours, and then allowed to stand overnight. Water was added, and the mixture was subjected to extraction with hexane. The extract was washed with water, with an alkaline aqueous solution and with a saturated sodium chloride aqueous solution, and dried over anhydrous sodium sulfate. The dried extract was concentrated and purified by distillation. Boiling point 78° C. (44 Torr). Yield 32%.

(2) Production of 4'-methoxybutyloxybiphenyl-4-carboxylic acid 7.2 Grams of 1-bromo-4-methoxybutane and 4.5 g of 4'-hydroxybiphenyl-4-carboxylic acid were refluxed in 100 ml of water and 400 ml of ethanol for 4 hours. Concentrated hydrochloric acid was added to the reaction mixture so that the mixture showed pH 1, then 150 ml of water was added, and the resultant mixture was refluxed for 1 hour. The reaction mixture was cooled to precipitate a crystal, and the crystal was recovered by filtration. The so-obtained crystal was recrystallized from acetone. Yield 61%.

(3) Production of 4-(1-trifluoromethyl-6-ethoxyhexyloxycarbonylphenyl) 4'-methoxybutyloxbiphenyl-4-carboxylate 0.9 Gram of 4'-methoxybutyloxybiphenyl-4-carboxylic acid, 0.82 g of 4-hydroxy-1-trifluoromethyl-6-ethoxyhexyloxycarbonylphenyl 0.05 g of dimethylaminopyridine were dissolved in 10 ml of tetrahydrofuran. A solution of 0.6 g of dicyclohexylcarbodiimide (DCC) in 5 ml of tetrahydrofuran was added dropwise, and the mixture was stirred at room temperature for 4 hours.

Tetrahydrofuran was distilled off, and the residue was subjected to a silica gel column for separation and purification to give the intended product. Yield 50%.

Figure 12:
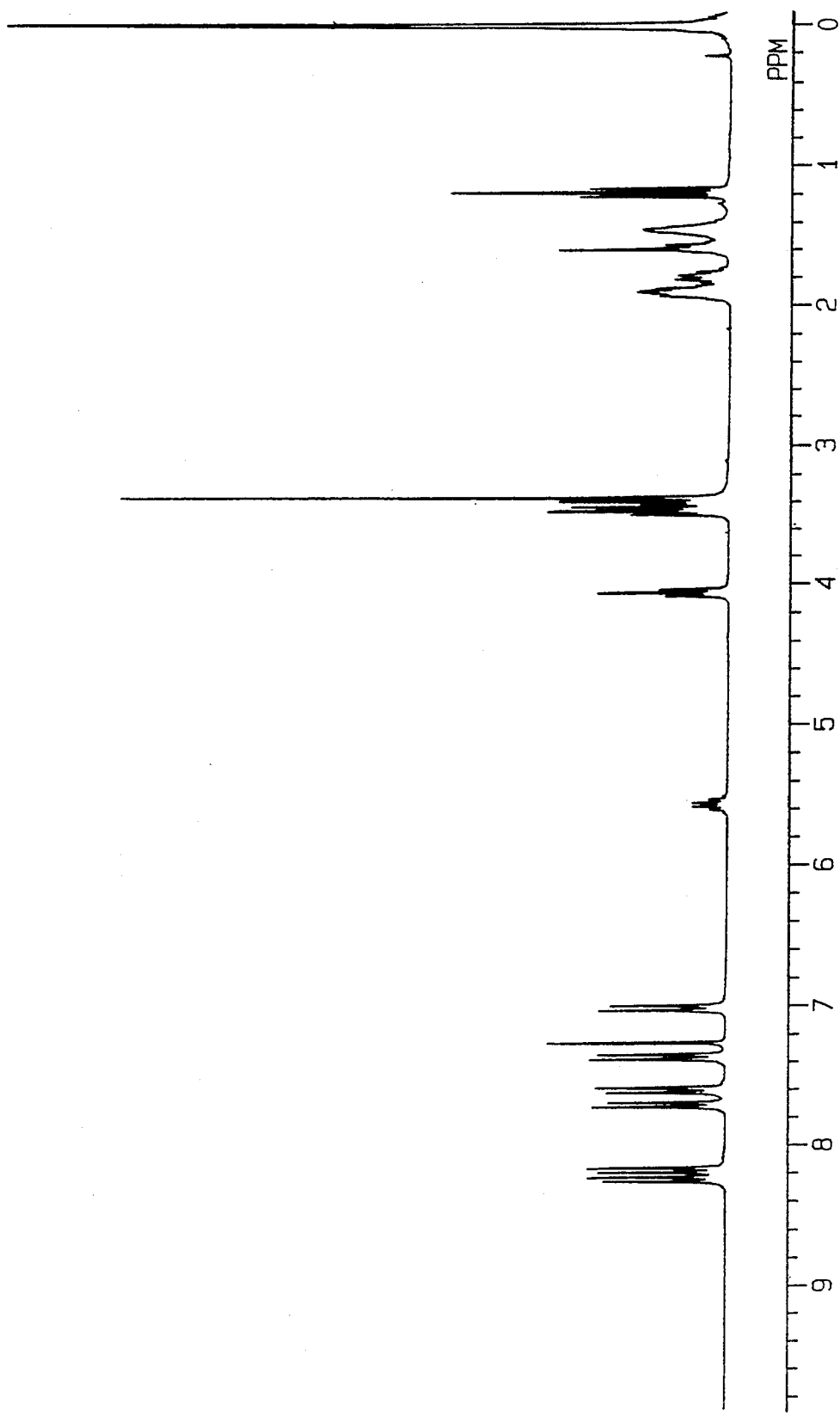

FIG. 12 shows the NMR spectrum of the above product. The phase identification was carried out by texture observation and DSC measurement.

The phase sequence of the above-obtained compound was as follows. This compound had an anti-ferroelectric phase and hence, was found to be a liquid crystal having an anti-ferroelectric phase.

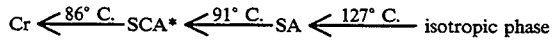

EXAMPLE 12

Production of 3-fluoro-4-(1-trifluoromethyl-6-ethoxyhexyloxycarbonylphenyl) 4'-methoxybutyloxybiphenyl-4-caraboxylate (compound of the formula (I) in which p=4, X=H, Y=F, Z=CF$_3$, q=5, m=1 and n=2)

The above compound was produced in the same manner as in Example 11 except that the 4-hydroxy-1-trifluoromethyl-6-ethoxyloxycarbonylphenyl was replaced with 3-fluoro-4-hydroxy-1-trifluoromethyl-6-ethoxyhexyloxycarbonylphenyl.

Figure 13:
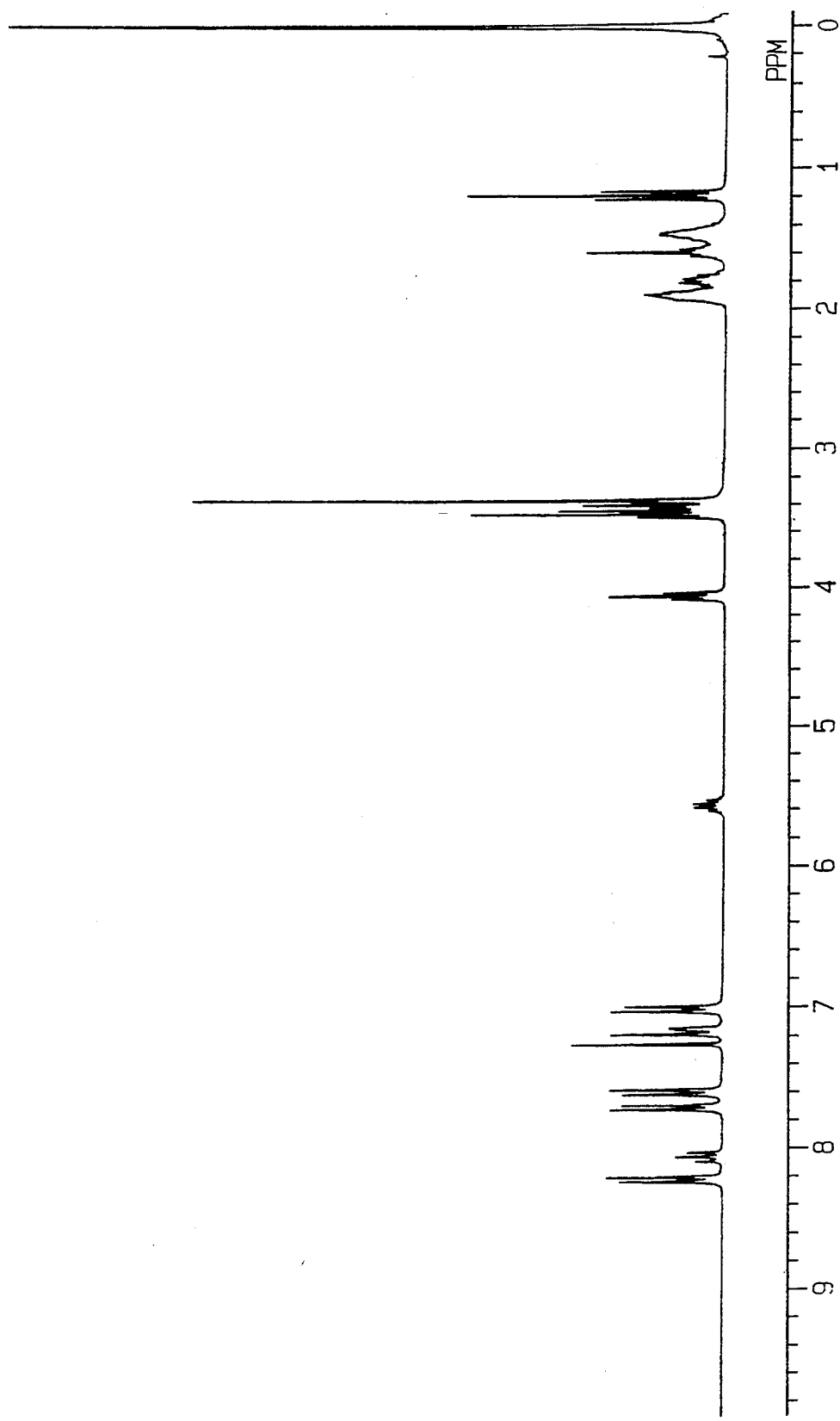

FIG. 13 shows the NMR spectrum of the above-obtained compound. The phase identification was carried out by texture observation and DSC measurement.

The phase sequence of the above-obtained compound was as follows. This compound had an anti-ferroelectric phase and hence, was found to be a liquid crystal having an anti-ferroelectric phase.

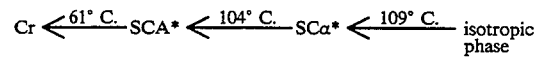

In the above phase sequence, SCα* is a phase similar to an anti-ferroelectric phase but not identified. When measured at 67° C., the above compound showed a very fast response time. That is, the response time from an anti-ferroelectric phase to a ferroelectric phase was 4 microseconds, and the response time from a ferroelectric phase to an anti-ferroelectric phase was 4 microseconds.

EXAMPLE 13

Production of 3-fluoro-4-(1-trifluoromethyheptyloxycarabonylphenyl) 4'-methoxybutyloxybiphenyl-4-carboxylate (compound of the formula (I) in which p=4, X=H, Y=F, Z=CF$_3$, q=0, m=0 and n=6)

The above compound was produced in the same manner as in Example 12 except that the 3-fluoro-4-hydroxy-1-trifluoromethyl-6-ethoxyhexyloxycarbonylphenyl was replaced with 3-fluoro-4-hydroxy-1-trifluoromethyl-6-heptyloxycarbonylphenyl.

Figure 14:
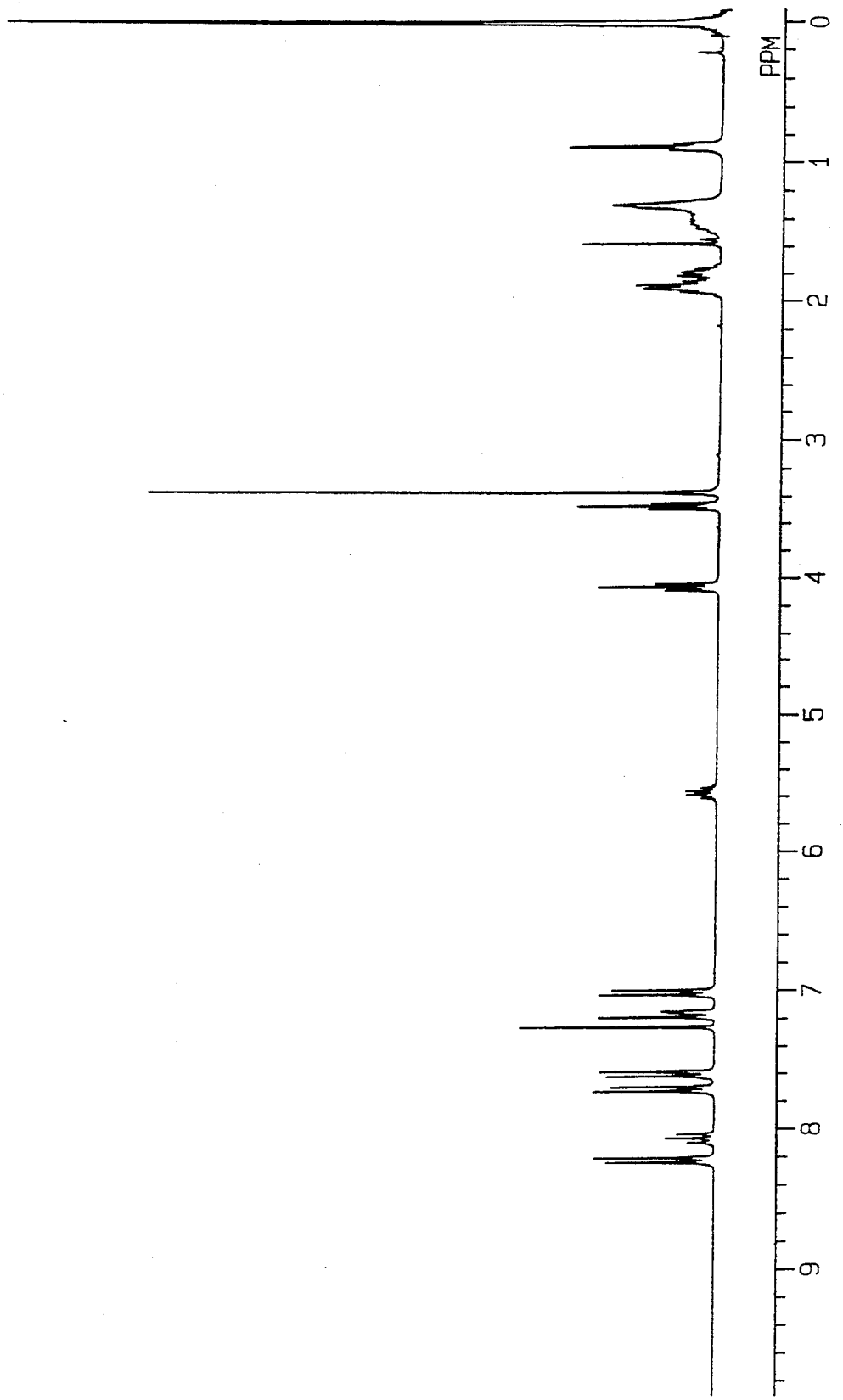

FIG. 14 shows the NMR spectrum of the above-obtained compound. The phase identification was carried out by texture observation and DSC measurement.

The phase sequence of the above-obtained compound was as follows. This compound had an anti-ferroelectric phase and hence, was found to be a liquid crystal having an anti-ferroelectric phase.

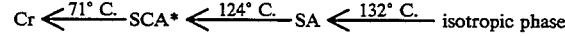

When measured at 104° C., the above compound showed a very fast response time. That is, the response time from an anti-ferroelectric phase to a ferroelectric phase was 4 microseconds, and the response time from a ferroelectric phase to an anti-ferroelectric phase was 4 microseconds.

EXAMPLE 14

Production of 3-fluoro-4-(1-methylheptyloxycarbonylphenyl) 4'-methoxyoctyloxybiphenyl-4-carboxylate (compound of the formula (I) in which p=8, X=H, Y=F, Z=CH$_3$, q=0, m=0 and n=6)

A liquid crystal was produced in the same manner as in Example 8 except that the 4'- methoxyhexyloxybiphenyl-4-carboyxlic acid and 3-fluoro-4-hydroxy-1-methylpentyloxycarbonylphenyl were replaced with 4'-methoxyoctyloxybiphenyl-4-carboxylic acid and 3-fluoro-4-hydroxy-1-methylheptyloxycarbonylphenyl.

Figure 15:
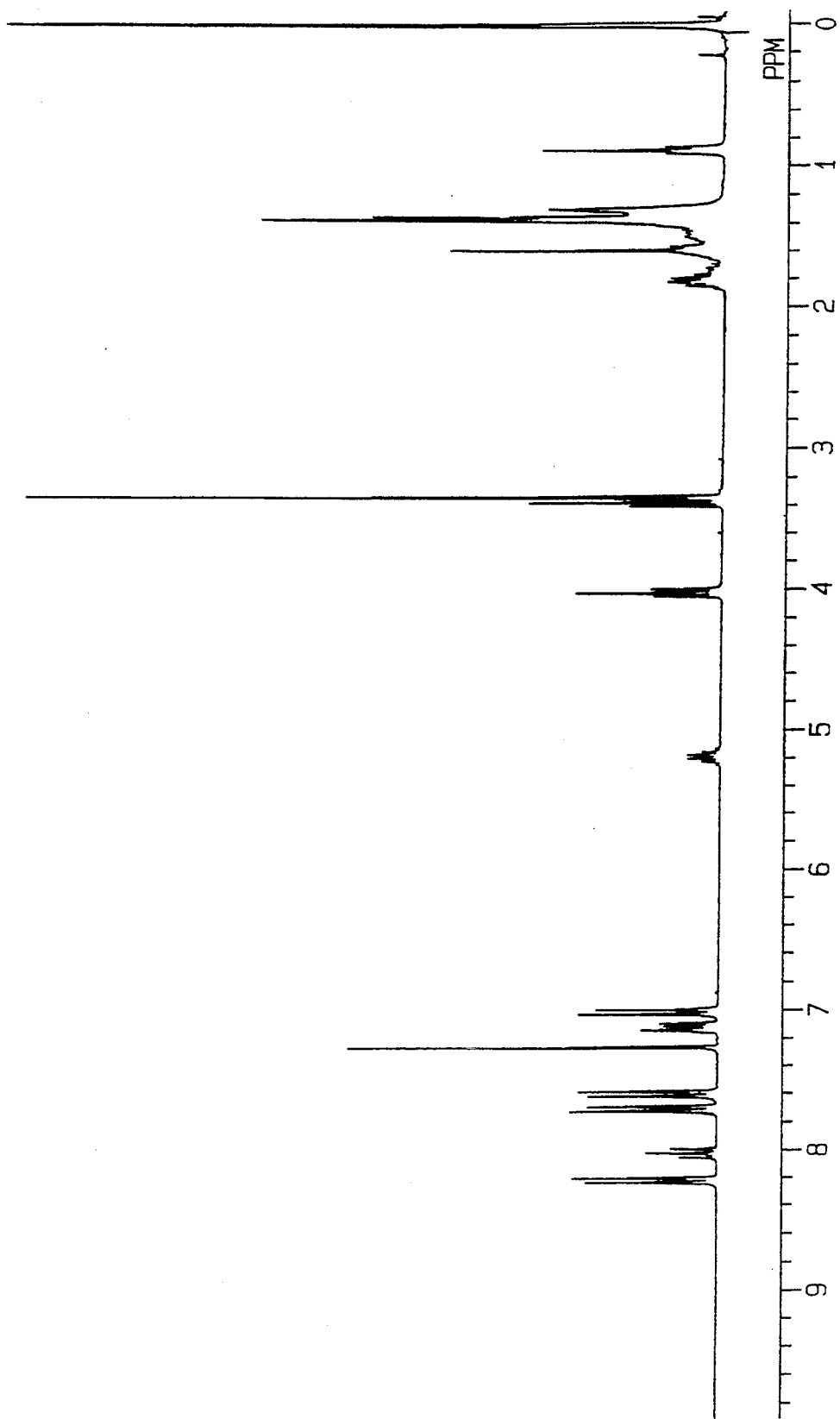

FIG. 15 shows the NMR spectrum of the above-obtained liquid crystal.

The phase sequence of the above-obtained liquid crystal was as follows.

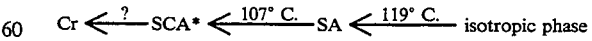

When the above compound was evaluated for an optical response in the same manner as in Example 1, item (5), double hysteresis peculiar to an anti-ferroelectric phase was found at a temperature of 108° C. or lower. Further, the above compound was measured for a response time in the same manner as in Example 1, item (5), to show very fast response characteristics.

That is, the response time from an anti-ferroelectric phase to a ferroelectric phase at 96° C. was 144 microseconds, and the response time from a ferroelectric phase to an anti-ferroelectric phase at 96° C. was 76 microseconds.

EXAMPLE 15

Production of 3-fluoro-4-(1-trifuoromethylheptyloxycarbonylphenyl) 4'-methoxyoctyloxybiphenyl-4-carboxylate (compound of the formula (I) in which p=8, X=H, Y=F, Z=CF$_3$, q=0, m=0 and n=6)

A liquid crystal was produced in the same manner as in Example 14 except that the 3-fluoro-4-hydroxy-1-methylheptyloxycarbonylphenyl was replaced with 3-fluoro-4-hydroxy-1-trifluoromethylheptyloxcarbonyl.

Figure 16:
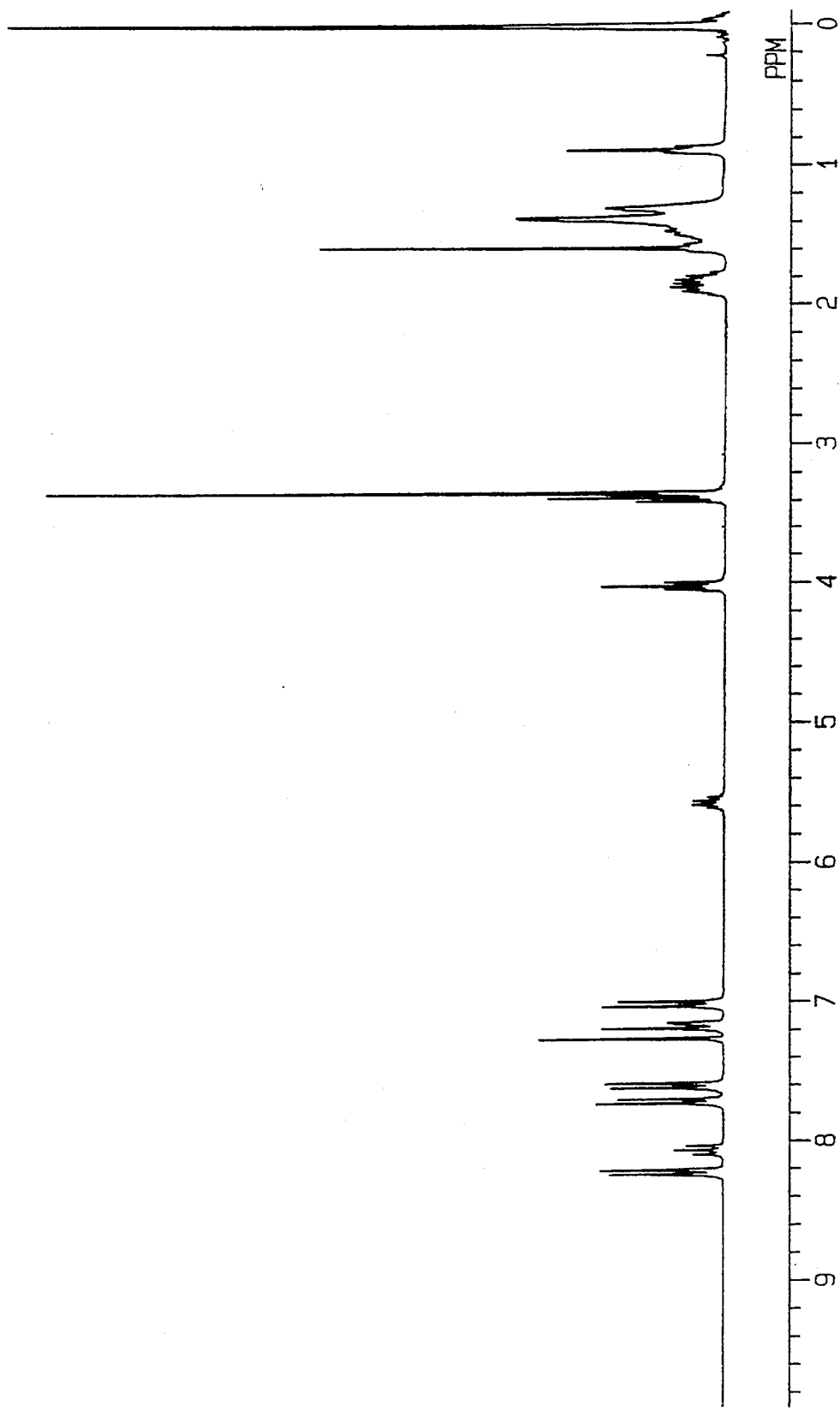

FIG. 16 shows the NMR spectrum of the above-obtained liquid crystal.

The phase sequence of the above-obtained liquid crystal was as follows.

Cr $\xleftarrow{?}$ SCA* $\xleftarrow{90° C.}$ isotropic phase

When the above compound was evaluated for an optical response in the same manner as in Example 1, item (5), double hysteresis peculiar to an anti-ferroelectric phase was found at a temperature of 90° C. or lower. Further, the above compound was measured for a response time in the same manner as in Example 1, item (5), to show very fast response characteristics. That is, the response time from an anti-ferroelectric phase to a ferroelectric phase at 80° C. was 99 microseconds, and the response time from a ferroelectric phase to an anti-ferroelectric phase at 80° C. was 47 microseconds.

EXAMPLE 16

Production of 3-fluoro-4-(1-trifluoromethylheptyloxycarbonylphenyl) 4'-methoxyoctyloxybiphenyl-4-carboxylate (compound of the formula (I) in which p=8, X=H, Y=F, Z=CF$_3$, q=5, m=1 and n=2)

A liquid crystal was produced in the same manner as in Example 14 except that the 3-fluoro-4-hydroxy-1-methylheptyloxycarbonylphenyl was replaced with 3-fluoro-4-hydroxy-1-trifluoromethyl-6-ethoxyheptyloxycarbonyl.

Figure 17:
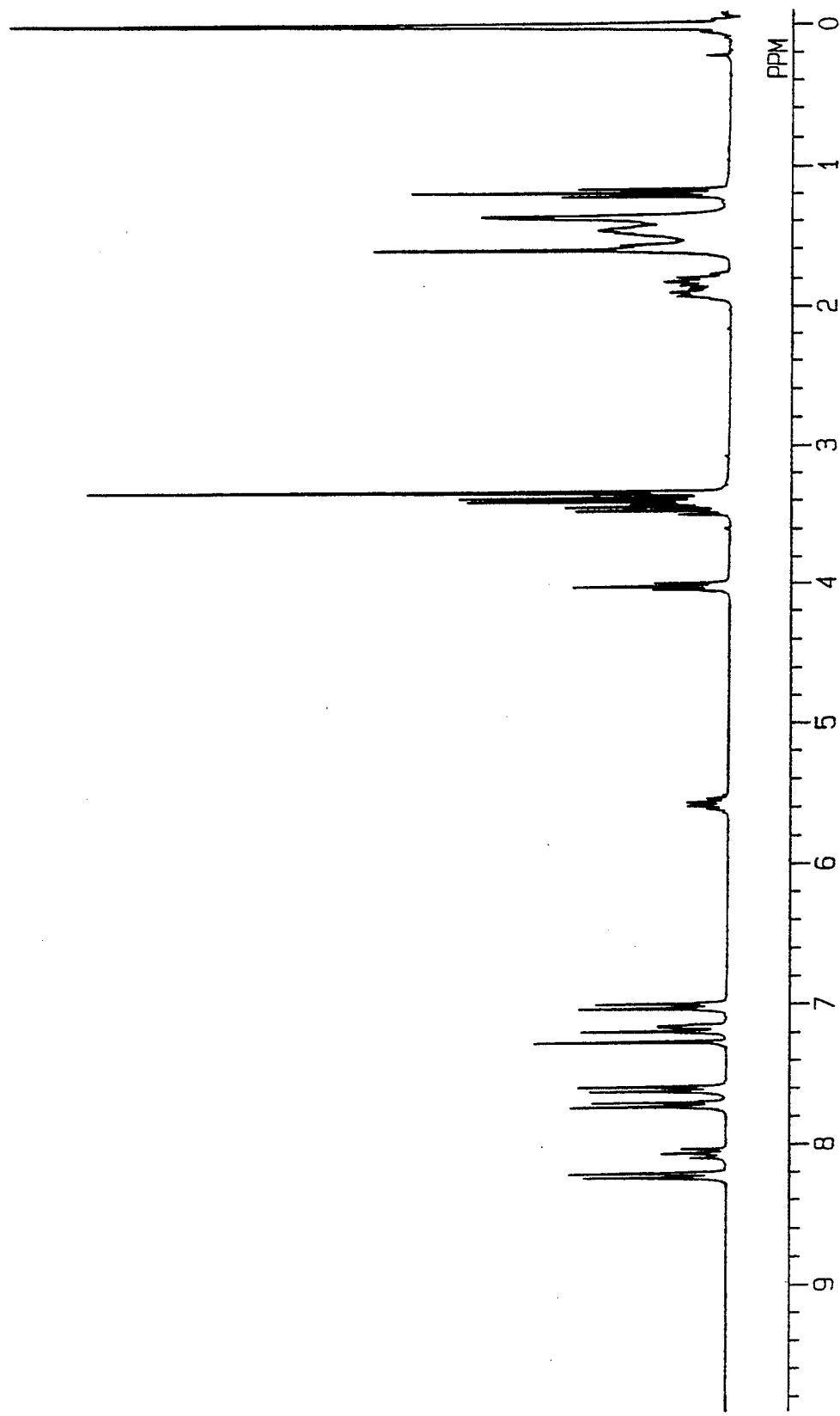
Figure 18:
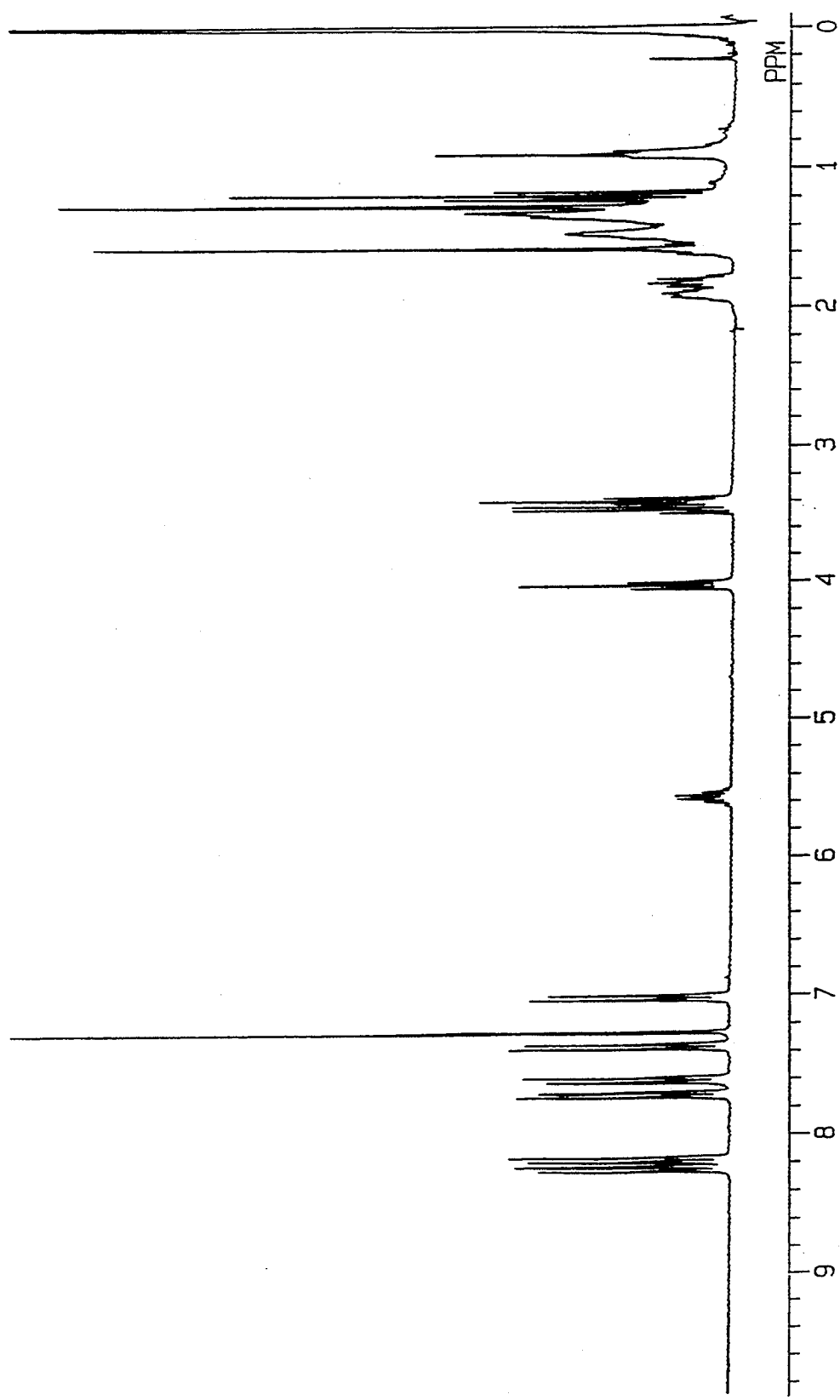
FIGS. 18 to 24 show the NMR spectra of the liquid crystals obtained in Comparative Examples 1 to 7.
Figure 19:
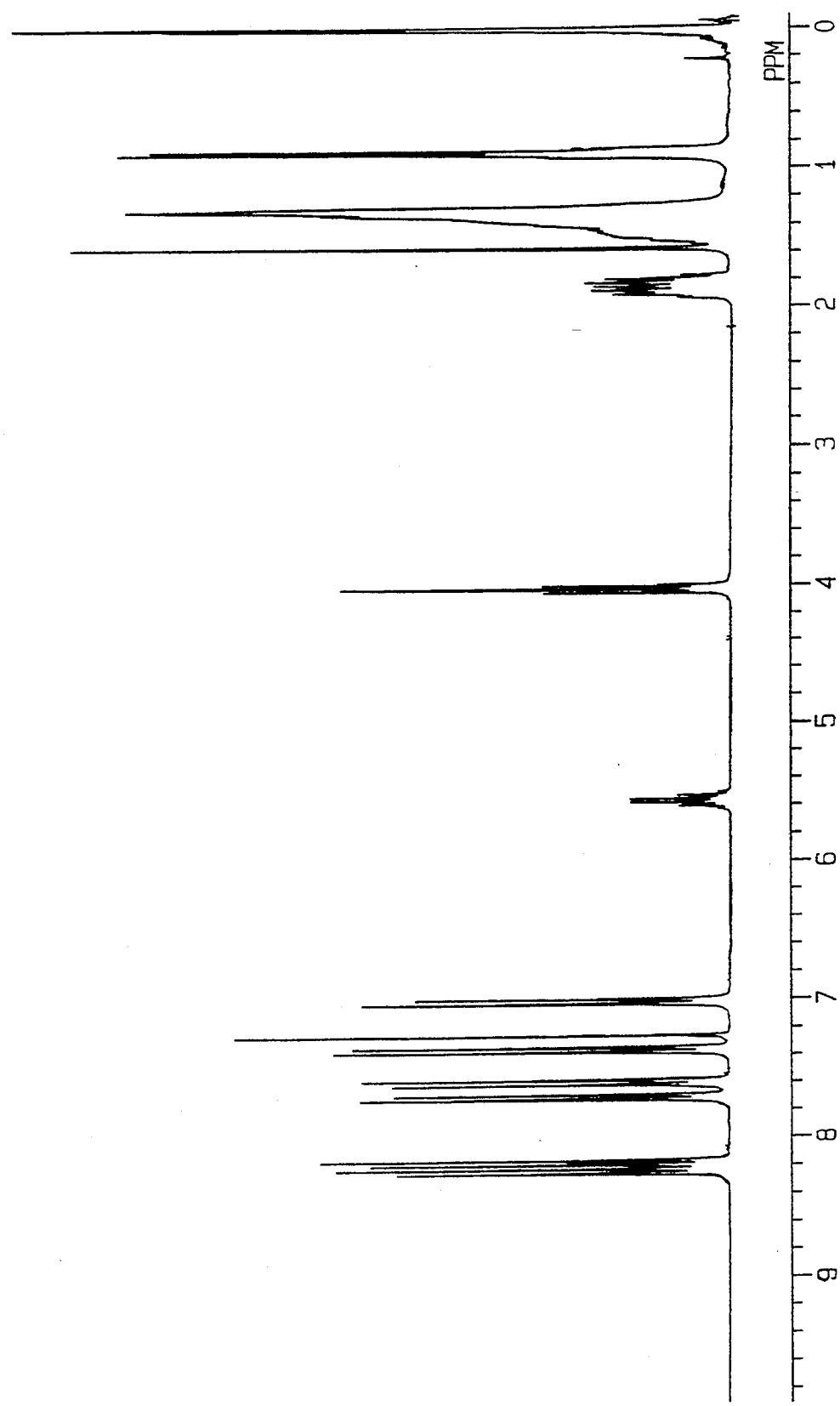
Figure 20:
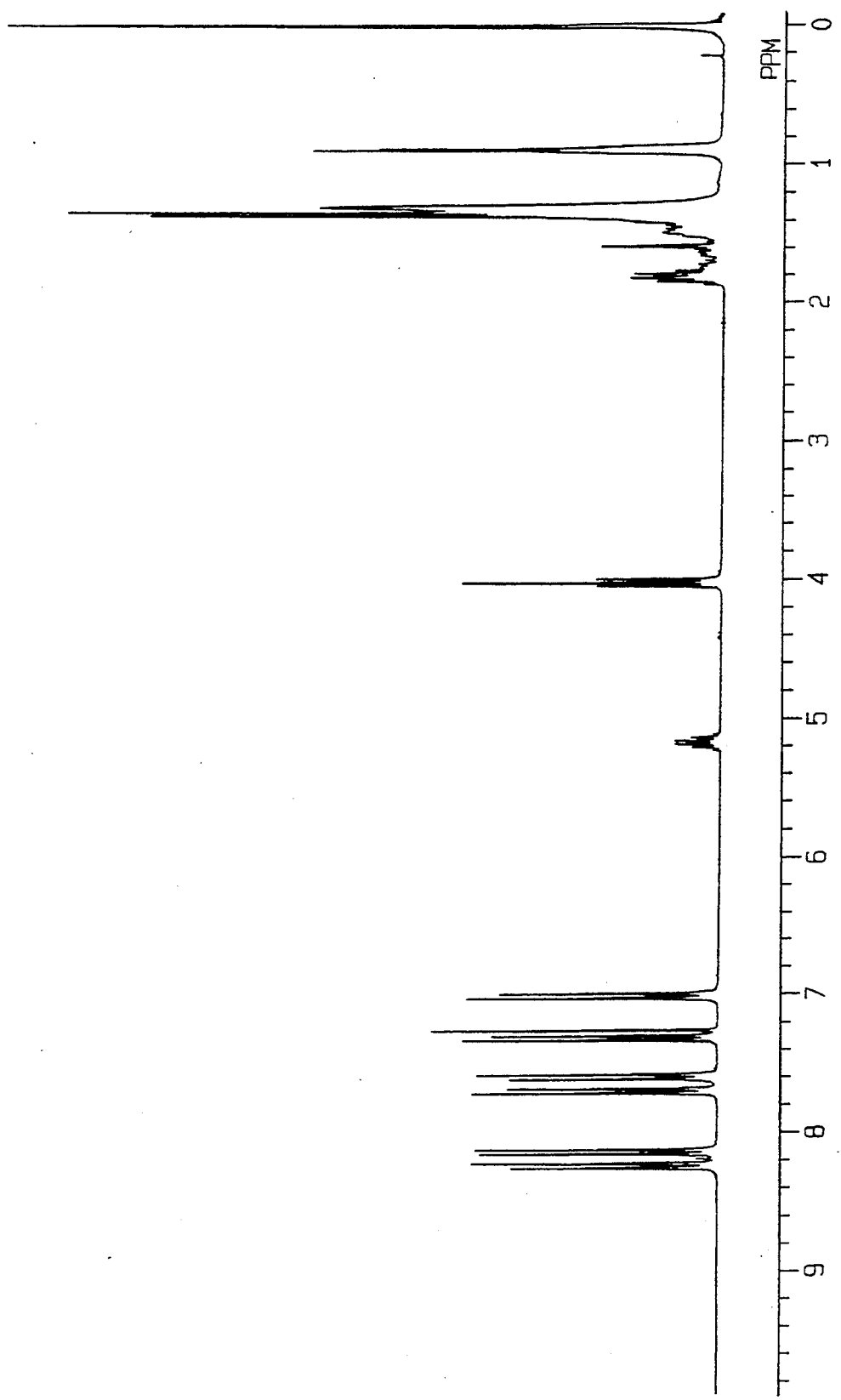
Figure 21:
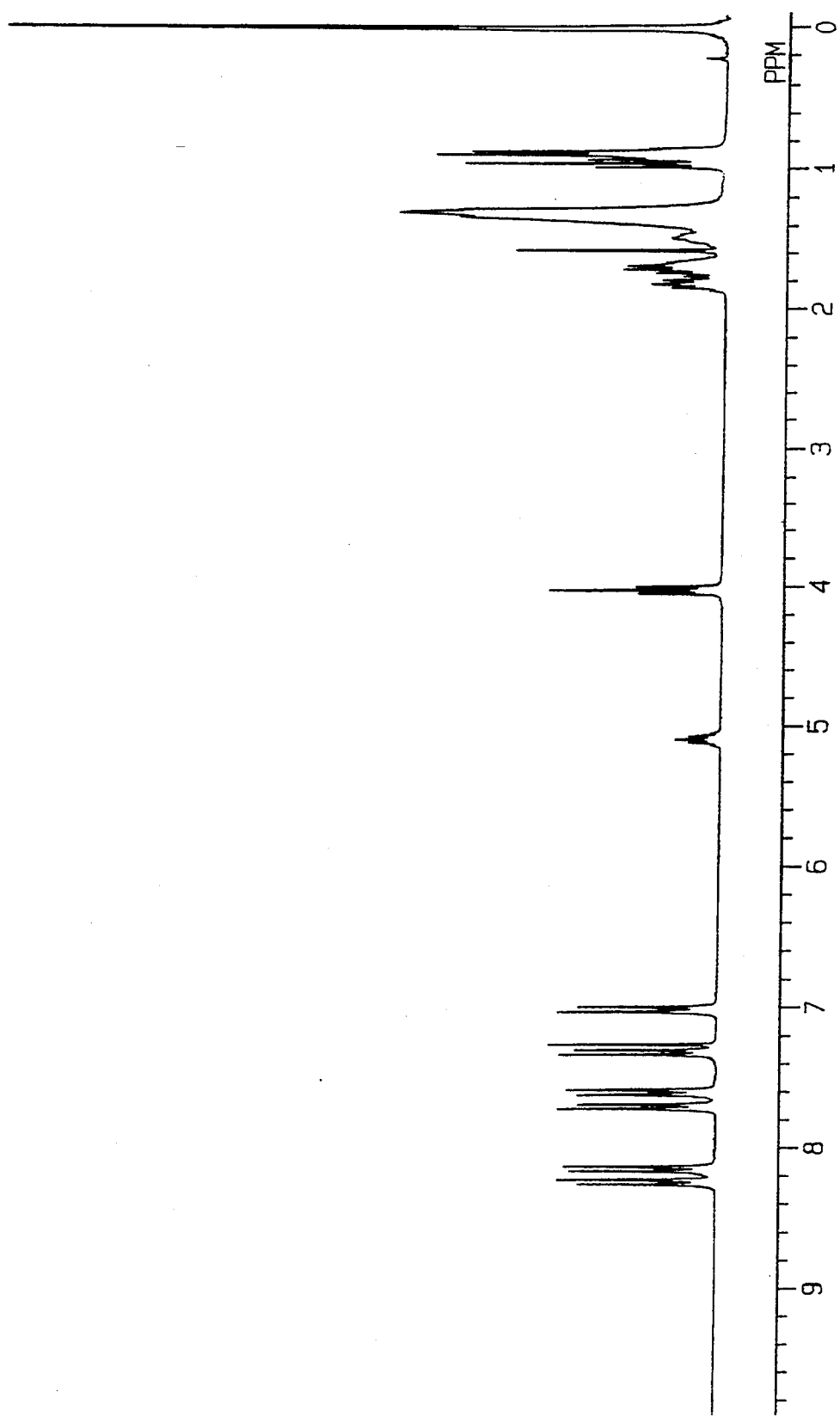

FIG. 17 shows the NMR spectrum of the above-obtained liquid crystal.

The phase sequence of the above-obtained liquid crystal was as follows.

Cr $\xleftarrow{?}$ SCA* $\xleftarrow{72° C.}$ isotropic phase

When the above compound was evaluated for an optical response in the same manner as in Example 1, item (5), double hysteresis peculiar to an anti-ferroelectric phase was found at a temperature of 108° C. or lower. Further, the above compound was measured for a response time in the same manner as in Example 1, item (5), to show very fast response characteristics. That is, the response time from an anti-ferroelectric phase to a ferroelectric phase at 60° C. was 18 microseconds, and the response time from a ferroelectric phase to an anti-ferroelectric phase at 60° C. was 88 microseconds.

COMPARATIVE EXAMPLES 1–4

Liquid crystals having the same optically active groups as those of the liquid crystals obtained in Examples 1 to 4 were synthesized in the same manner as in Examples 1 to 4 except that the 4'-methoxyhexyloxybiphenyl-4-carboxylic acid was replaced with 4'-octyloxybiphenyl-4-carboxylic acid.

FIGS. 18 to 21 show the NMR spectra of the above-obtained liquid crystals. Table 3 shows the results of their physical property measurements.

TABLE 3

| Physical properties in C$_8$H$_{17}$—O—Ph—Ph—COO—Ph—COO—R* | | |
|---|---|---|
| R* | Phase sequence | Response time μ second |
| CEx. 1<br>—C*H(CF$_3$)(CH$_2$)$_5$OC$_2$H$_5$ | CR $\xleftarrow{45° C.}$ SCA* $\xleftarrow{96° C.}$ SA $\xleftarrow{103° C.}$ Iso | 8,89<br>(85° C.) |
| CEx. 2<br>—C*H(CF$_3$)C$_6$H$_{13}$ | CR $\xleftarrow{69° C.}$ SCA* $\xleftarrow{114° C.}$ SA $\xleftarrow{123° C.}$ Iso | 24,36<br>(100° C.) |
| CEx. 3<br>—C*H(CH$_3$)C$_6$H$_{13}$ | CR $\xleftarrow{?}$ SIA* $\xleftarrow{69° C.}$ SCA* $\xleftarrow{117° C.}$ SC* $\xleftarrow{122° C.}$ SA $\xleftarrow{147° C.}$ Iso | 17,134<br>(100° C.) |
| CEx. 4 *1<br>—C*H(C$_2$H$_5$)C$_6$H$_{13}$ | CR $\xleftarrow{-3° C.}$ SCA* $\xleftarrow{91° C.}$ SA $\xleftarrow{105° C.}$ Iso | 1000,736<br>(80° C.) |

*1 The alkyl group C$_8$H$_{17}$ on the left hand side was replaced with C$_{10}$H$_{21}$.

COMPARATIVE EXAMPLES 5–7

Liquid crystals having the same optically active groups as those of the liquid crystals obtained in Examples 5 to 7 were synthesized in the same manner as in Examples 5 to 7 except that the 4'-methoxyhexyloxybiphenyl-4-carboxylic acid was replaced with 4'-octyloxybiphenyl-4-carboxylic acid.

Figure 22:
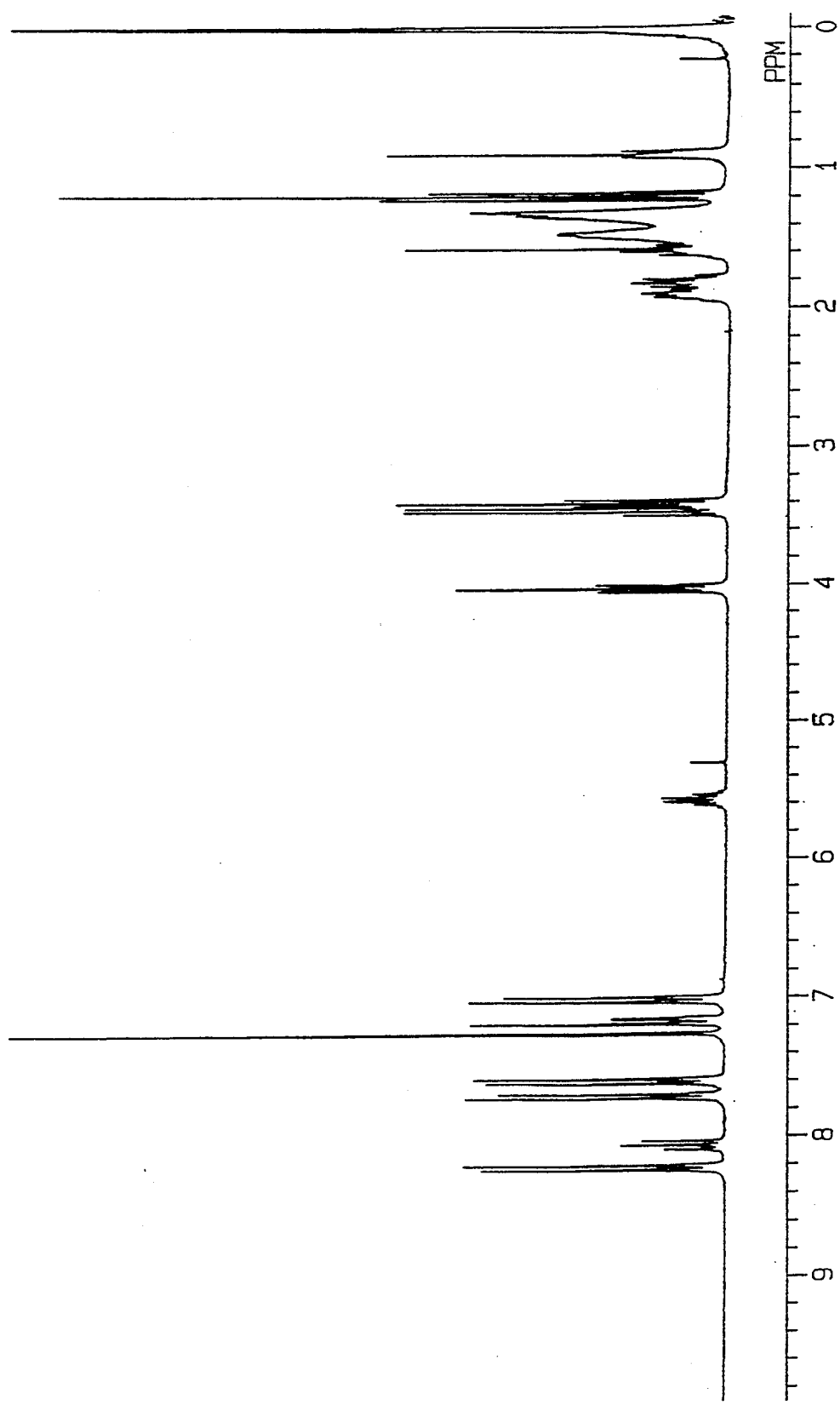
Figure 23:
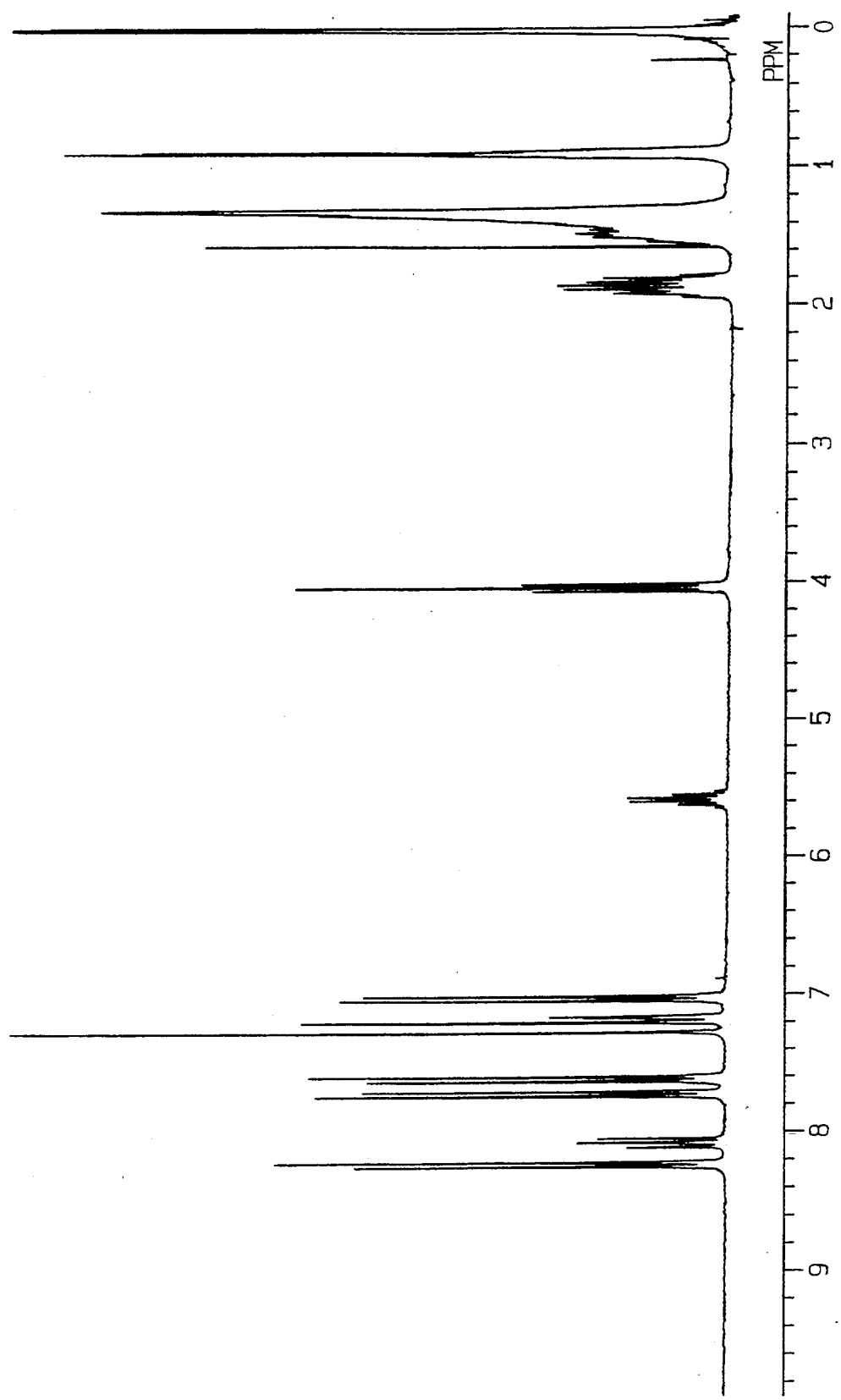
Figure 24:
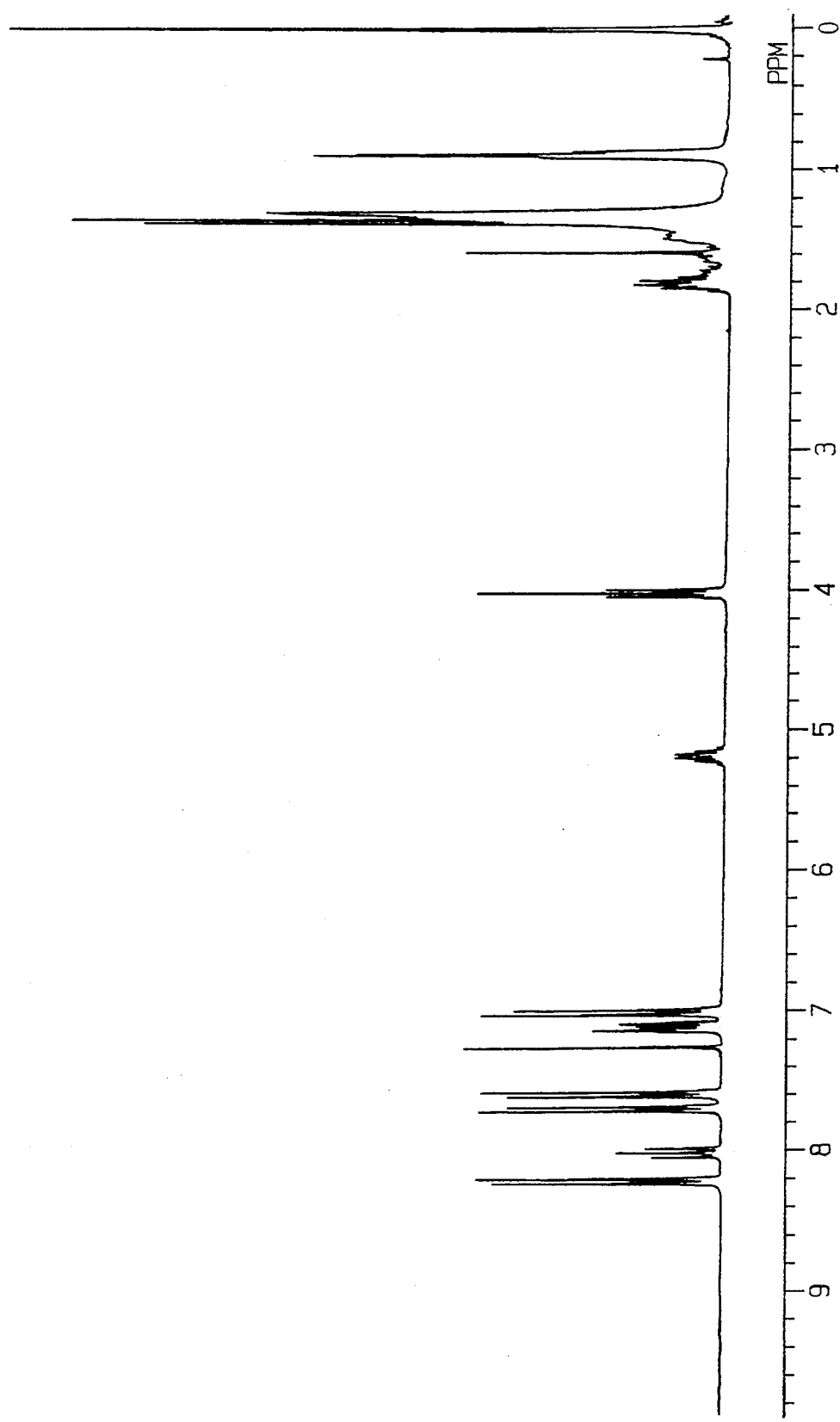

FIGS. 22 to 24 show the NMR spectra of the above-obtained liquid crystals. Table 4 shows the results of their physical property measurements.

TABLE 4

| Physical properties in C$_8$H$_{17}$—O—Ph—Ph—COO—Ph(3-F)—COO—R* | | |
|---|---|---|
| R* | Phase sequence | Response time μ second |
| CEx. 5<br>—C*H(CF$_3$)(CH$_2$)$_5$OC$_2$H$_5$ | CR $\xleftarrow{?}$ SCA* $\xleftarrow{90° C.}$ Iso | 40,400<br>(80° C.) |

TABLE 4-continued

Physical properties in C$_8$H$_{17}$—O—Ph—Ph—COO—Ph(3-F)—COO—R*

| R* | Phase sequence | Response time μ second |
|---|---|---|
| CEx. 6 —C*H(CF$_3$)C$_6$H$_{13}$ | CR ←?— SX ←10° C.— SCA* ←108° C.— SA ←110° C.— Iso | 200,400 (95° C.) |
| CEx. 7 —C*H(CH$_3$)C$_6$H$_{13}$ | CR ←?— SIA* ←20 C.— SCA* ←121° C.— SA ←140° C.— Iso | 170,214 (110° C.) |

What is claimed is:

1. An anti-ferroelectric liquid crystal of the formula (I),

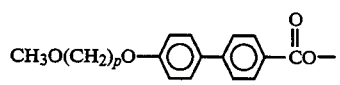

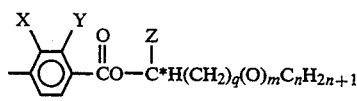

wherein
is an integer of 3 to 8,
each of X and Y is independently a hydrogen atom or a fluorine atom,
Z is —CF$_3$, —CH$_3$ or —C$_2$H$_5$,
q is 0 or 5,
m is 0 or 1,
n is an integer of 2 to 8, and
C* is an asymmetric carbon. provided that when m is 0, q is 0 and n is an integer of 4 to 8 and that when m is 1, q is 5 and z is —CF$_3$.

2. The anti-ferroelectric liquid crystal of claim 1, wherein Z in the formula (I) is —CF$_3$ or —CH$_3$.

3. The anti-ferroelectric liquid crystal of claim 1 or 2, wherein p in the formula (I) is 4, 6 or b 8.

4. The anti-ferroelectric liquid crystal of claim 1 or 2, wherein the formula (I) X is a hydrogen atom and Y is a hydrogen atom or a fluorine atom.

5. The anti-ferroelectric liquid crystal of claim 1, wherein in the formula (I) m is 1, q is 5, z is —CF$_3$ and n is 2.

6. The anti-ferroelectric liquid crystal of claim 5, wherein in the formula (I) X is a hydrogen atom and Y is a hydrogen atom or a fluorine atom.

7. The anti-ferroelectric liquid crystal of claim 5 or 6, wherein in the formula (I) p is 4, 6 or 8.

8. The anti-ferroelectric liquid crystal of claim 1, wherein the formula (I) m and q are both zero, Z is —CF$_3$ or —CH$_3$ and n is 4 or 6.

9. The anti-ferroelectric liquid crystal of claim 8, wherein in the formula (I) n is 6.

10. The anti-ferroelectric liquid crystal of claim 8 or 9, wherein in the formula (I) X is a hydrogen atom and Y is a hydrogen atom or a fluorine atom.

11. A liquid crystal display device to which the anti-ferroelectric liquid crystal recited in claim 1 is applied.

12. The anti-ferroelectric liquid crystal of claim 3, wherein in the formula (I) X is a hydrogen atom and Y is a hydrogen atom or a fluorine atom.

13. An anti-ferroelectric liquid crystal of the formula (I),

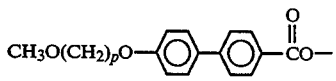

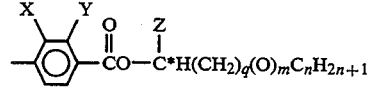

wherein
p is an integer of 3 to 8,
each of X and Y is independently a hydrogen atom or a fluorine atom,
Z is —CF$_3$,
q is 5,
m is 1,
n is an integer of 2 to 8, and
C* is an asymmetric carbon.

14. The anti-ferroelectric liquid crystal of claim 13, wherein p in the formula (I) is 4, 6 or 8.

15. The anti-ferroelectric liquid crystal of claim 13 or 14, wherein in the formula (I) X is a hydrogen atom and Y is a hydrogen atom or a fluorine atom.

16. The anti-ferroelectric liquid crystal of claim 15, wherein in the formula (I) n is 2.

17. The anti-ferroelectric liquid crystal of claim 16 wherein in the formula (I) X is a hydrogen atom and Y is a hydrogen atom or a fluorine atom.

18. The anti-ferroelectric liquid crystal of claim 15 or 16, wherein in the formula (I) p is 4, 6 or 8.

19. An anti-ferroelectric liquid crystal of the formula (I),

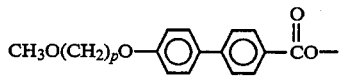

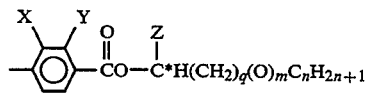

wherein
p is an integer of 3 to 8,
each of X and Y is independently a hydrogen atom or a fluorine atom,
Z is —CF$_3$, —CH$_3$ or —C$_2$H$_5$,
m is 0,
q is 0,
n is an integer of 4 to 8, and
C* is an asymmetric carbon.

20. The anti-ferroelectric liquid crystal of claim 19, wherein p in the formula (I) is 4, 6 or 8.

21. The anti-ferroelectric liquid crystal of claims 19 and 20, wherein in the formula (I) X is a hydrogen atom and Y is a hydrogen atom or a fluorine atom.

22. The anti-ferroelectric liquid crystal of claim 19, wherein in the formula (I) Z is —CF$_3$ or —CH$_3$ and n is 4 or 6.

23. The anti-ferroelectric liquid crystal of claim 22 wherein in the formula (I) n is 6.

24. The anti-ferroelectric liquid crystal of claim 22 or 23, wherein in the formula (I) X is a hydrogen atom and Y is a hydrogen atom or a fluorine atom.

* * * * *